(12) United States Patent
Eder et al.

(10) Patent No.: US 7,942,874 B2
(45) Date of Patent: *May 17, 2011

(54) APPARATUS FOR TISSUE CAUTERIZATION

(75) Inventors: Joseph Eder, Los Altos, CA (US);
Camran Nezhat, Woodside, CA (US);
Benjamin Theodore Nordell, II, San Mateo, CA (US)

(73) Assignee: Aragon Surgical, Inc., Palo Alto, CA (US)

( * ) Notice: Subject to any disclaimer, the term of this patent is extended or adjusted under 35 U.S.C. 154(b) by 686 days.

This patent is subject to a terminal disclaimer.

(21) Appl. No.: 11/382,652

(22) Filed: May 10, 2006

(65) Prior Publication Data
US 2006/0259034 A1   Nov. 16, 2006

Related U.S. Application Data

(60) Provisional application No. 60/725,720, filed on Oct. 11, 2005, provisional application No. 60/680,937, filed on May 12, 2005.

(51) Int. Cl.
*A61B 18/14* (2006.01)
(52) U.S. Cl. ............... 606/50; 606/51; 606/52; 606/42; 606/41; 606/38
(58) Field of Classification Search ............. 606/41–52, 606/205–207
See application file for complete search history.

(56) References Cited

U.S. PATENT DOCUMENTS

| | | |
|---|---|---|
| 3,356,408 A | 12/1967 | Stutz |
| 3,845,771 A | 11/1974 | Vise |
| 3,920,021 A | 11/1975 | Hittenbrandt |
| 4,041,952 A | 8/1977 | Morrison et al. |
| 4,492,231 A | 1/1985 | Auth |
| 4,532,924 A | 8/1985 | Auth et al. |
| 4,671,274 A | 6/1987 | Sorochenko |
| 4,972,846 A | 11/1990 | Owens et al. |
| 4,998,527 A | 3/1991 | Meyers |
| 5,037,379 A | 8/1991 | Clayman et al. |
| 5,078,736 A | 1/1992 | Behl |
| 5,151,102 A | 9/1992 | Kamiyama |
| 5,178,618 A | 1/1993 | Kanadarpa |

(Continued)

FOREIGN PATENT DOCUMENTS

CA   2061215   2/1992

(Continued)

OTHER PUBLICATIONS

Abu-Rustum, NR, et al.; Transperitoneal Laparoscopic Pelvic And Para-Aortic Lymph Node Dissection Using The Argon-Beam Coagulator And Monopolar Instruments: An 8-Year Study And Description Of Technique; Gynecol Oncol. Jun. 2003; 89 (3): 504-13; Memorial Sloan-Kettering Cancer Center, 1275 York Avenue, New York, NY 10021, USA. gynbreast@mskcc.org.

(Continued)

*Primary Examiner* — Michael Peffley
*Assistant Examiner* — Ronald Hupczey, Jr.
(74) *Attorney, Agent, or Firm* — Shay Glenn LLP

(57) ABSTRACT

The invention is concerned with cauterizing and resecting tissue. A pair of electrodes are placed on opposed tissue surfaces, and radio frequency power is applied through the electrodes to cauterizing a tissue mass therebetween. After cauterization has been effected, the tissue may be resected along a plane within the cauterized region with minimum or no bleeding. The tissue mass may then be removed.

22 Claims, 4 Drawing Sheets

U.S. PATENT DOCUMENTS

| | | | |
|---|---|---|---|
| 5,190,541 A | 3/1993 | Abele et al. | |
| 5,207,691 A | 5/1993 | Nardella | |
| 5,217,030 A | 6/1993 | Yoon | |
| 5,250,074 A | 10/1993 | Wilk et al. | |
| 5,267,998 A | 12/1993 | Hagen | |
| 5,269,780 A | 12/1993 | Roos | |
| 5,269,782 A | 12/1993 | Sutter | |
| 5,273,524 A | 12/1993 | Fox et al. | |
| 5,277,201 A | 1/1994 | Stern | |
| 5,281,216 A | 1/1994 | Klicek | |
| 5,282,799 A | 2/1994 | Rydell | |
| 5,290,287 A | 3/1994 | Boebel et al. | |
| 5,295,990 A | 3/1994 | Levin | |
| 5,300,087 A | 4/1994 | Knoepfler | |
| 5,324,289 A | 6/1994 | Eggers | |
| 5,330,471 A | 7/1994 | Eggers | |
| 5,330,502 A | 7/1994 | Hassler et al. | |
| 5,336,229 A | 8/1994 | Noda | |
| 5,336,237 A | 8/1994 | Chin et al. | |
| 5,341,807 A * | 8/1994 | Nardella | 600/381 |
| 5,342,381 A | 8/1994 | Tidemand | |
| 5,352,223 A | 10/1994 | McBrayer et al. | |
| 5,352,235 A | 10/1994 | Koros et al. | |
| 5,374,277 A | 12/1994 | Hassler et al. | |
| 5,377,415 A | 1/1995 | Gibson | |
| 5,391,166 A | 2/1995 | Eggers | |
| 5,395,369 A | 3/1995 | McBrayer et al. | |
| 5,396,900 A | 3/1995 | Slater et al. | |
| 5,403,312 A | 4/1995 | Yates et al. | |
| 5,417,687 A | 5/1995 | Nadella et al. | |
| 5,423,814 A | 6/1995 | Zhu et al. | |
| 5,443,463 A | 8/1995 | Stern et al. | |
| 5,443,470 A | 8/1995 | Stern et al. | |
| 5,445,638 A | 8/1995 | Rydell et al. | |
| 5,447,513 A | 9/1995 | Davison et al. | |
| 5,449,355 A | 9/1995 | Rhum et al. | |
| 5,456,684 A | 10/1995 | Schmidt et al. | |
| 5,458,598 A | 10/1995 | Feinberg et al. | |
| 5,462,546 A | 10/1995 | Rydell | |
| 5,472,442 A | 12/1995 | Klicek | |
| 5,482,054 A | 1/1996 | Slater et al. | |
| 5,484,435 A | 1/1996 | Fleenor et al. | |
| 5,484,436 A | 1/1996 | Eggers et al. | |
| 5,496,312 A * | 3/1996 | Klicek | 606/34 |
| 5,496,317 A | 3/1996 | Goble et al. | |
| 5,514,134 A | 5/1996 | Rydell et al. | |
| 5,531,744 A | 7/1996 | Nardella et al. | |
| 5,540,684 A | 7/1996 | Hassler, Jr. | |
| 5,540,685 A | 7/1996 | Parins et al. | |
| 5,542,945 A | 8/1996 | Fritzsch | |
| 5,549,606 A | 8/1996 | McBrayer et al. | |
| 5,549,637 A | 8/1996 | Crainich | |
| 5,556,397 A | 9/1996 | Long et al. | |
| 5,558,100 A | 9/1996 | Cox | |
| 5,558,671 A | 9/1996 | Yates | |
| 5,562,700 A | 10/1996 | Huitema et al. | |
| 5,562,701 A | 10/1996 | Huitema et al. | |
| 5,562,702 A | 10/1996 | Huitema et al. | |
| 5,562,720 A | 10/1996 | Stern et al. | |
| 5,564,615 A | 10/1996 | Bishop et al. | |
| 5,569,243 A | 10/1996 | Kortenbach | |
| 5,571,100 A | 11/1996 | Goble et al. | |
| 5,573,535 A | 11/1996 | Viklund | |
| 5,578,052 A | 11/1996 | Koros et al. | |
| 5,599,350 A | 2/1997 | Schulze et al. | |
| 5,601,224 A | 2/1997 | Bishop et al. | |
| 5,603,700 A | 2/1997 | Daneshvar | |
| 5,611,803 A | 3/1997 | Heaven | |
| 5,624,452 A | 4/1997 | Yates | |
| 5,637,110 A | 6/1997 | Pennybacker | |
| 5,637,111 A | 6/1997 | Sutcu et al. | |
| 5,653,692 A | 8/1997 | Masterson et al. | |
| 5,658,281 A | 8/1997 | Heard | |
| 5,662,662 A | 9/1997 | Bishop et al. | |
| 5,665,085 A | 9/1997 | Nardella | |
| 5,665,100 A | 9/1997 | Yoon | |
| 5,667,526 A | 9/1997 | Levin | |
| 5,669,907 A | 9/1997 | Platt et al. | |
| 5,673,840 A | 10/1997 | Schulze et al. | |
| 5,673,841 A | 10/1997 | Schulze et al. | |
| 5,674,184 A | 10/1997 | Hassler, Jr. | |
| 5,674,220 A | 10/1997 | Fox et al. | |
| 5,680,982 A | 10/1997 | Schulze et al. | |
| 5,681,282 A | 10/1997 | Eggers et al. | |
| 5,683,385 A | 11/1997 | Kortenbach | |
| 5,683,388 A | 11/1997 | Slater | |
| 5,688,270 A | 11/1997 | Yates et al. | |
| 5,693,051 A | 12/1997 | Schulze et al. | |
| 5,697,949 A | 12/1997 | Guirtino et al. | |
| 5,700,261 A | 12/1997 | Brikerhoff | |
| 5,702,390 A | 12/1997 | Austin et al. | |
| 5,704,534 A | 1/1998 | Huitema et al. | |
| 5,707,369 A | 1/1998 | Vatekunas et al. | |
| 5,709,680 A | 1/1998 | Yates et al. | |
| 5,713,896 A | 2/1998 | Nadella et al. | |
| 5,715,832 A | 2/1998 | Koblish et al. | |
| 5,718,703 A | 2/1998 | Chin | |
| 5,728,143 A | 3/1998 | Gough et al. | |
| 5,733,283 A | 3/1998 | Malis et al. | |
| 5,735,289 A | 4/1998 | Pfeffer et al. | |
| 5,735,848 A | 4/1998 | Yates et al. | |
| 5,735,849 A | 4/1998 | Baden et al. | |
| 5,741,285 A | 4/1998 | McBrayer | |
| 5,743,906 A | 4/1998 | Parins et al. | |
| 5,755,717 A | 5/1998 | Yates et al. | |
| 5,769,849 A | 6/1998 | Eggers | |
| 5,776,130 A | 7/1998 | Buysse et al. | |
| 5,797,906 A | 8/1998 | Rhum et al. | |
| 5,810,811 A | 9/1998 | Yates et al. | |
| 5,817,092 A | 10/1998 | Behl | |
| 5,823,066 A | 10/1998 | Huitema et al. | |
| 5,833,689 A | 11/1998 | Long | |
| 5,833,690 A | 11/1998 | Yates et al. | |
| 5,855,576 A | 1/1999 | LeVeen et al. | |
| 5,860,975 A | 1/1999 | Goble et al. | |
| 5,891,142 A | 4/1999 | Eggers et al. | |
| 5,954,720 A | 9/1999 | Wilson et al. | |
| 6,003,517 A | 12/1999 | Sheffield et al. | |
| 6,004,319 A | 12/1999 | Goble et al. | |
| 6,030,384 A | 2/2000 | Nezhat | |
| 6,050,995 A | 4/2000 | Durgin | |
| 6,056,744 A | 5/2000 | Edwards | |
| 6,056,746 A | 5/2000 | Goble et al. | |
| 6,066,139 A | 5/2000 | Ryan et al. | |
| 6,068,626 A | 5/2000 | Harrington et al. | |
| 6,074,386 A | 6/2000 | Goble et al. | |
| 6,086,586 A | 7/2000 | Hooven | |
| 6,090,106 A | 7/2000 | Goble et al. | |
| 6,093,186 A | 7/2000 | Goble | |
| 6,096,037 A | 8/2000 | Mulier et al. | |
| 6,099,550 A | 8/2000 | Yoon | |
| 6,123,701 A * | 9/2000 | Nezhat | 606/33 |
| 6,152,920 A | 11/2000 | Thompson et al. | |
| 6,162,220 A | 12/2000 | Nezhat | |
| 6,174,309 B1 | 1/2001 | Wrublewski et al. | |
| 6,179,832 B1 | 1/2001 | Jones et al. | |
| 6,203,541 B1 | 3/2001 | Keppel | |
| 6,206,877 B1 | 3/2001 | Kese et al. | |
| 6,228,084 B1 | 5/2001 | Kirwan, Jr. | |
| 6,277,114 B1 | 8/2001 | Bullivant et al. | |
| 6,283,963 B1 | 9/2001 | Regula | |
| 6,287,304 B1 * | 9/2001 | Eggers et al. | 606/37 |
| 6,293,946 B1 | 9/2001 | Thorne | |
| 6,306,134 B1 | 10/2001 | Goble et al. | |
| 6,312,430 B1 | 11/2001 | Wilson et al. | |
| 6,322,494 B1 | 11/2001 | Bullivant et al. | |
| 6,361,559 B1 | 3/2002 | Hauser et al. | |
| 6,364,879 B1 | 4/2002 | Chen et al. | |
| 6,371,956 B1 | 4/2002 | Wilson et al. | |
| 6,391,029 B1 | 5/2002 | Hooven et al. | |
| 6,398,779 B1 | 6/2002 | Buysse et al. | |
| 6,416,509 B1 | 7/2002 | Goble et al. | |
| 6,440,130 B1 | 8/2002 | Mulier et al. | |
| 6,443,952 B1 | 9/2002 | Mulier et al. | |
| 6,464,702 B2 | 10/2002 | Schulze et al. | |
| 6,485,486 B1 | 11/2002 | Trembly et al. | |
| 6,485,489 B2 | 11/2002 | Teirstein et al. | |

| | | | | | | |
|---|---|---|---|---|---|---|
| 6,491,690 B1 | 12/2002 | Goble et al. | | 7,588,566 B2 | 9/2009 | Treat et al. |
| 6,494,881 B1 | 12/2002 | Bales et al. | | 2001/0029367 A1 | 10/2001 | Fleenor et al. |
| 6,514,252 B2 | 2/2003 | Nezhat et al. | | 2002/0107514 A1 | 8/2002 | Hooven |
| 6,517,530 B1 | 2/2003 | Kleven | | 2002/0128643 A1* | 9/2002 | Simpson et al. .............. 606/34 |
| 6,520,185 B1 | 2/2003 | Bommannan et al. | | 2002/0151882 A1 | 10/2002 | Marko et al. |
| 6,533,784 B2 | 3/2003 | Truckai et al. | | 2002/0183738 A1 | 12/2002 | Chee et al. |
| 6,554,829 B2 | 4/2003 | Schulze et al. | | 2003/0018331 A1 | 1/2003 | Dycus et al. |
| 6,564,806 B1 | 5/2003 | Fogarty et al. | | 2003/0078577 A1 | 4/2003 | Truckai et al. |
| 6,565,560 B1 | 5/2003 | Goble et al. | | 2003/0158547 A1 | 8/2003 | Phan |
| 6,565,561 B1 | 5/2003 | Goble et al. | | 2003/0199869 A1 | 10/2003 | Johnson et al. |
| 6,584,360 B2 | 6/2003 | Francischelli | | 2003/0229344 A1 | 12/2003 | Dycus et al. |
| 6,610,060 B2 | 8/2003 | Mulier et al. | | 2004/0049185 A1 | 3/2004 | Latterell et al. |
| 6,613,048 B2 | 9/2003 | Mulier et al. | | 2004/0068274 A1 | 4/2004 | Hooven |
| 6,616,654 B2 | 9/2003 | Mollenauer | | 2004/0097919 A1 | 5/2004 | Wellman et al. |
| 6,616,659 B1 | 9/2003 | de la Torre et al. | | 2004/0122423 A1 | 6/2004 | Dycus et al. |
| 6,623,482 B2 | 9/2003 | Pendekanti et al. | | 2004/0236320 A1 | 11/2004 | Protsenko et al. |
| 6,626,901 B1 | 9/2003 | Treat et al. | | 2004/0236326 A1 | 11/2004 | Schulze et al. |
| 6,645,198 B1 | 11/2003 | Bommannan et al. | | 2005/0010212 A1 | 1/2005 | McClurken et al. |
| 6,645,201 B1 | 11/2003 | Utley et al. | | 2005/0015085 A1 | 1/2005 | McClurken et al. |
| 6,648,839 B2 | 11/2003 | Manna | | 2005/0021024 A1 | 1/2005 | Hooven |
| 6,652,518 B2 | 11/2003 | Wellman | | 2005/0021026 A1 | 1/2005 | Baily |
| 6,656,177 B2 | 12/2003 | Truckai et al. | | 2005/0033277 A1 | 2/2005 | Clague et al. |
| 6,676,660 B2 | 1/2004 | Wampler et al. | | 2005/0033278 A1 | 2/2005 | McClurken et al. |
| 6,682,526 B1 | 1/2004 | Jones et al. | | 2005/0033282 A1 | 2/2005 | Hooven |
| 6,682,527 B2 | 1/2004 | Strul | | 2005/0070895 A1 | 3/2005 | Ryan et al. |
| 6,695,840 B2 | 2/2004 | Schulze | | 2005/0070978 A1* | 3/2005 | Bek et al. ...................... 607/101 |
| 6,722,371 B1 | 4/2004 | Fogarty et al. | | 2005/0090819 A1 | 4/2005 | Goble |
| 6,726,682 B2 | 4/2004 | Harrington et al. | | 2005/0107781 A1 | 5/2005 | Ostrovsky et al. |
| 6,736,814 B2 | 5/2004 | Manna et al. | | 2005/0113820 A1 | 5/2005 | Goble et al. |
| 6,743,229 B2 | 6/2004 | Buysse et al. | | 2005/0113826 A1 | 5/2005 | Johnson et al. |
| 6,752,154 B2 | 6/2004 | Fogarty et al. | | 2005/0119654 A1 | 6/2005 | Swanson et al. |
| 6,752,803 B2 | 6/2004 | Goldman et al. | | 2005/0131390 A1 | 6/2005 | Heinrich et al. |
| 6,755,827 B2 | 6/2004 | Mulier et al. | | 2005/0137591 A1 | 6/2005 | Barry et al. |
| 6,770,070 B1 | 8/2004 | Balbierz | | 2005/0171530 A1 | 8/2005 | Hooven |
| 6,773,435 B2 | 8/2004 | Schulze et al. | | 2005/0171533 A1 | 8/2005 | Latterell et al. |
| 6,776,780 B2 | 8/2004 | Mulier et al. | | 2005/0187561 A1 | 8/2005 | Lee-Sepsick et al. |
| 6,808,525 B2 | 10/2004 | Latterell et al. | | 2005/0192568 A1 | 9/2005 | Truckai et al. |
| 6,821,273 B2 | 11/2004 | Mollenauer | | 2005/0192633 A1 | 9/2005 | Montpetit |
| 6,837,888 B2 | 1/2005 | Ciarrocca et al. | | 2005/0203500 A1 | 9/2005 | Saadat et al. |
| 6,840,938 B1 | 1/2005 | Morley et al. | | 2005/0256522 A1* | 11/2005 | Francischelli et al. .......... 606/41 |
| 6,843,789 B2 | 1/2005 | Goble | | 2006/0025812 A1 | 2/2006 | Shelton |
| 6,852,108 B2 | 2/2005 | Barry et al. | | 2006/0041254 A1 | 2/2006 | Francischelli et al. |
| 6,858,028 B2 | 2/2005 | Mulier et al. | | 2006/0052778 A1 | 3/2006 | Chapman et al. |
| 6,889,089 B2 | 5/2005 | Behl et al. | | 2006/0064085 A1 | 3/2006 | Schechter et al. |
| 6,893,435 B2 | 5/2005 | Goble | | 2006/0142751 A1 | 6/2006 | Treat et al. |
| 6,896,673 B2 | 5/2005 | Hooven | | 2006/0167451 A1 | 7/2006 | Cropper |
| 6,902,536 B2 | 6/2005 | Manna et al. | | 2006/0189980 A1 | 8/2006 | Johnson et al. |
| 6,908,463 B2 | 6/2005 | Treat et al. | | 2006/0190029 A1 | 8/2006 | Wales |
| 6,913,579 B2 | 7/2005 | Truckai et al. | | 2006/0199999 A1 | 9/2006 | Ikeda et al. |
| 6,918,909 B2 | 7/2005 | Ohyama et al. | | 2006/0217709 A1 | 9/2006 | Couture et al. |
| 6,923,803 B2 | 8/2005 | Goble | | 2006/0226196 A1 | 10/2006 | Hueil et al. |
| 6,923,806 B2 | 8/2005 | Hooven et al. | | 2006/0229665 A1 | 10/2006 | Wales et al. |
| 6,929,642 B2 | 8/2005 | Xiao et al. | | 2006/0258954 A1 | 11/2006 | Timberlake et al. |
| 6,936,048 B2 | 8/2005 | Hurst | | 2006/0259035 A1 | 11/2006 | Nezhat |
| 6,953,461 B2 | 10/2005 | McClurken et al. | | 2006/0271038 A1 | 11/2006 | Johnson et al. |
| 6,981,628 B2 | 1/2006 | Wales | | 2006/0271042 A1 | 11/2006 | Latterell et al. |
| 7,063,699 B2 | 6/2006 | Hess et al. | | 2006/0287674 A1 | 12/2006 | Ginn et al. |
| 6,918,907 B2 | 7/2006 | Ohyama et al. | | 2006/0289602 A1 | 12/2006 | Wales et al. |
| 7,090,637 B2 | 8/2006 | Danitz et al. | | 2007/0055231 A1 | 3/2007 | Dycus et al. |
| 7,090,673 B2 | 8/2006 | Dycus et al. | | 2007/0062017 A1 | 3/2007 | Dycus et al. |
| 7,090,685 B2 | 8/2006 | Kortenbach et al. | | 2007/0073340 A1 | 3/2007 | Shelton et al. |
| 7,101,371 B2 | 9/2006 | Dycus et al. | | 2007/0129726 A1 | 6/2007 | Eder et al. |
| 7,101,372 B2 | 9/2006 | Dycus et al. | | 2007/0179497 A1 | 8/2007 | Eggers et al. |
| 7,101,373 B2 | 9/2006 | Dycus et al. | | 2007/0208330 A1 | 9/2007 | Treat et al. |
| 7,118,587 B2 | 10/2006 | Dycus et al. | | 2007/0250113 A1 | 10/2007 | Hegeman et al. |
| 7,125,409 B2 | 10/2006 | Truckai et al. | | 2007/0260242 A1 | 11/2007 | Dycus et al. |
| 7,250,048 B2* | 7/2007 | Francischelli et al. .......... 606/32 | | 2007/0299439 A1 | 12/2007 | Latterell et al. |
| 7,255,697 B2 | 8/2007 | Dycus et al. | | 2008/0039835 A1 | 2/2008 | Johnson et al. |
| 7,267,677 B2 | 9/2007 | Johnson et al. | | 2008/0045947 A1 | 2/2008 | Johnson et al. |
| 7,270,664 B2 | 9/2007 | Johnson et al. | | 2008/0114356 A1 | 5/2008 | Johnson et al. |
| 7,276,068 B2 | 10/2007 | Johnson et al. | | 2008/0188844 A1 | 8/2008 | McGreevy et al. |
| 7,278,991 B2 | 10/2007 | Morris et al. | | 2008/0195093 A1 | 8/2008 | Couture et al. |
| 7,291,143 B2 | 11/2007 | Swanson | | 2008/0275446 A1 | 11/2008 | Messerly |
| 7,329,256 B2 | 2/2008 | Johnson et al. | | 2009/0018535 A1 | 1/2009 | Schechter et al. |
| 7,364,577 B2 | 4/2008 | Wham et al. | | 2009/0138006 A1 | 5/2009 | Bales et al. |
| 7,367,972 B2* | 5/2008 | Francischelli et al. .......... 606/34 | | 2009/0149853 A1 | 6/2009 | Shields et al. |
| 7,410,483 B2 | 8/2008 | Danitz et al. | | 2009/0171354 A1 | 7/2009 | Deville et al. |
| 7,513,898 B2 | 4/2009 | Johnson et al. | | | | |
| 7,540,872 B2 | 6/2009 | Schechter et al. | | | | |

| | | |
|---|---|---|
| 2009/0234347 A1 | 9/2009 | Treat et al. |
| 2009/0240245 A1 | 9/2009 | Deville et al. |
| 2009/0299367 A1 | 12/2009 | Ginnebaugh et al. |

FOREIGN PATENT DOCUMENTS

| | | |
|---|---|---|
| EP | 487269 | 5/1991 |
| EP | 440385 | 7/1991 |
| EP | 502268 | 9/1992 |
| EP | 562195 | 9/1993 |
| EP | 658333 | 6/1995 |
| EP | 536998 | 4/1996 |
| EP | 518230 | 5/1996 |
| EP | 0737446 | 10/1996 |
| EP | 875209 | 4/1998 |
| EP | 878169 | 11/1998 |
| EP | 640315 | 12/1998 |
| EP | 923907 | 6/1999 |
| EP | 640317 | 9/1999 |
| EP | 771176 | 7/2000 |
| EP | 1050278 | 11/2000 |
| EP | 1064886 | 1/2001 |
| EP | 833593 | 2/2001 |
| EP | 1254637 | 11/2002 |
| EP | 1293169 | 3/2003 |
| EP | 1293170 | 3/2003 |
| EP | 869742 | 5/2003 |
| EP | 1330989 | 7/2003 |
| EP | 1330991 | 7/2003 |
| EP | 1344498 | 9/2003 |
| EP | 873089 | 10/2003 |
| EP | 742696 | 11/2003 |
| EP | 959784 | 4/2004 |
| EP | 0794735 | 7/2004 |
| EP | 1004277 | 7/2004 |
| EP | 959786 | 9/2004 |
| EP | 913126 | 10/2004 |
| EP | 956827 | 10/2004 |
| EP | 1472984 | 11/2004 |
| EP | 1025807 | 12/2004 |
| EP | 1486177 | 12/2004 |
| EP | 1518498 | 3/2005 |
| EP | 1518499 | 3/2005 |
| EP | 927543 | 4/2005 |
| EP | 1532933 | 5/2005 |
| EP | 1621146 | 2/2006 |
| EP | 1632192 | 3/2006 |
| EP | 1637086 | 3/2006 |
| EP | 1645237 | 4/2006 |
| EP | 1747761 | 1/2007 |
| EP | 1852081 | 11/2007 |
| EP | 1862138 | 12/2007 |
| EP | 1958583 | 8/2008 |
| EP | 2065006 | 6/2009 |
| EP | 2106764 | 10/2009 |
| EP | 2110093 | 10/2009 |
| JP | A 11070123 | 3/1999 |
| JP | A 11070124 | 3/1999 |
| JP | A 2003/088534 | 3/2003 |
| JP | A 2004/049566 | 2/2004 |
| JP | A 2005/021703 | 1/2005 |
| JP | A 2005/144193 | 6/2005 |
| WO | WO 92/22257 | 12/1992 |
| WO | WO93/08754 | 5/1993 |
| WO | WO 94/00060 | 1/1994 |
| WO | WO 95/02371 | 1/1995 |
| WO | WO 95/14436 | 6/1995 |
| WO | WO 95/25471 | 9/1995 |
| WO | WO 96/05776 | 2/1996 |
| WO | WO9616605 | 6/1996 |
| WO | WO 96/23449 | 8/1996 |
| WO | WO 97/24073 | 7/1997 |
| WO | WO 97/24074 | 7/1997 |
| WO | WO 97/24995 | 7/1997 |
| WO | WO 98/12999 | 4/1998 |
| WO | WO 98/43548 | 10/1998 |
| WO | WO 98/53750 | 12/1998 |
| WO | WO 99/23933 | 5/1999 |
| WO | WO 99/51155 | 10/1999 |
| WO | WO 99/51158 | 10/1999 |
| WO | WO 99/52459 | 10/1999 |
| WO | WO 99/56646 | 11/1999 |
| WO | WO 00/13192 | 3/2000 |
| WO | WO 00/13193 | 3/2000 |
| WO | WO 00/47124 | 8/2000 |
| WO | WO0112090 | 2/2001 |
| WO | WO 01/35846 | 5/2001 |
| WO | WO 01/54602 | 8/2001 |
| WO | WO 01/58372 | 8/2001 |
| WO | WO 01/82812 | 11/2001 |
| WO | WO 02/24092 | 3/2002 |
| WO | WO 02/36028 | 5/2002 |
| WO | WO 02/067798 | 7/2002 |
| WO | WO 02/058542 | 8/2002 |
| WO | WO 02/071926 | 9/2002 |
| WO | WO 03/024348 | 3/2003 |
| WO | WO 03/096886 | 11/2003 |
| WO | WO 03/103522 | 12/2003 |
| WO | WO2004032596 | 4/2004 |
| WO | WO2004073490 | 9/2004 |
| WO | WO 2004/098383 | 11/2004 |
| WO | WO 2004/103156 | 12/2004 |
| WO | WO 2005/009213 | 2/2005 |
| WO | WO 2005/034729 | 4/2005 |
| WO | WO 2005/079901 | 9/2005 |
| WO | WO 2005/115251 | 12/2005 |
| WO | WO 2006/124601 | 11/2006 |
| WO | WO2006124518 | 11/2006 |
| WO | WO2008094564 | 8/2008 |
| WO | WO2009070780 | 6/2009 |
| WO | WO2009154976 | 12/2009 |

OTHER PUBLICATIONS

Aoki, T. et al.; *Thoracoscopic Resection Of The Lung With The Ultrasonic Scalpel*; Ann Thorac Surg. Apr. 1999; 67 (4): 1181-3; Department of Thoracic Surgery, Saiseikai Kanagawaken Hospital, Yokohama, Japan.

*Arthrocare Receives Clearance To Market Coblation-Based Devices For Gynecology And Laparoscopic Surgery; Clearance Includes Plasma Forceps And 21 Specific Indications*; Business Wire, p. 0524; Oct. 25, 2001.

Bergamaschi, R. et al.; Laparoscopic Intracorporeal Bowel Resection With Ultrasound Versus Electrosurgical Dissection; JSLS. Jan.-Mar. 2001; 5 (1): 17-20; National Center for Advanced Laparoscopic Surgery, Tondheim, Norway. r.bergamaschi@altavista.net.

Berguer, Ramon et al.; SAGES 2001 Hands-On Course I—Taking It To The Next Level: Advanced Laparoscopic Techniques; http://www.sages.org/01program/syllabi/ho1/ho1.html#schirme.

Briani, S. et al.; *Pseudo-Bipolar Electrocoagulation With A Branched Forceps*; Minerva Neurochir. 1967; 11 (3): 306-11.

Cakan, A. et al.; The Histological Effect Of Harmonic Scalpel And Electrocautery In Lung Resections. An Experimental Study In A Rat Model; J Cardiovasc Surg (Torino). Feb. 2004; 45 (1): 63-5; Department of Thoracic Surgery, Ege University School of Medicine, Izmir, Turkey. alpcakan@gohip.com.

Ceviker, N. et al.; *A New Coated Biploar Coagulator: Technical Note*; Acta Neurochir (Wein). 1998; 140 (6): 619-20; Department of Neurosurgery, Faculty of Medicine, Gazi University, Ankara, Turkey.

Cherchi, PL, et al.; *Utility Of Bipolar Electrocautery Scissors For Cervical Conization*; Eur J Gynaecol Oncol. 2002; 23 (2): 154-6; Department of Pharmacology, Gynecology and Obstetrics, University of Sassari, Italy.

*Circon Corporation—Company Report*; Investext p. 1-13; Jan. 3, 1995.

Colvin, D.P. et al.; *Development Of An Endoscopic RF Hyperthermia System For Deep Tumor Therapy*; American Society of Mechanical Engineers, Heat Transfer Division, (Publication) HTD v. 95. Publ by ASME (BED-v 7), New York, NY, USA p. 25-30; 1987.

Corson, S.L.; *Two New Laparoscopic Instruments: Bipolar Sterilizing Forceps And Uterine Manipulator*; Medical Instrumentation vol. 11, No. 1 p. 7-8; Jan.-Feb. 1977; USA.

*Curon Announces The Publication Of Data Supporting Durability And Effectiveness Of Stretta (R) System;—Positive One Year Follow-*

*Up Data Of U.S. Clinical Trial Published In Gastrointestinal Endoscopy*; PR Newswire, pNYTH10307022002; Feb. 7, 2002.

*Curon Medical Announces Presentation Of Positive Clinical Study Results Of Stretta(R) Procedure For Gastroesophageal Reflux Disease (GERD)*; PR Newswire, pNYW07920032002; Mar. 20, 2002.

Daniel, P. et al.; *Ultrasonic Sealing Of The Lung Parenchyma After Atypical Resection; Z Exp Chir Transplant Kunstliche Organe*. 1987; 20 (2): 117-21.

Digeronimo, EM et al.; *Cut-Blot-Coagulate: A New Time Saving Device*; Plast Reconstr Surg. Nov. 1982; 70 (5): 639-40.

Dubuc-Lissoir, J.; Use Of A New Energy-Based Vessel Ligation Device During Laparoscopic Gynecologic Oncologic Surgery; Surg Endosc. Mar. 2003; 17 (3): 466-8. Epub Oct. 31, 2002; Department of Obstetrics and Gynecology, CHUM—Notre-Dame Hospital, Pavillon Charles-Simard, 2065 Alexandre-de-Seve, 4th Floor, Montreal, Quebec, Canada, H2L 2W5. josee.dubuc-lissoir.chum@ssss.gouv.qc.ca.

Eichfeld U., et al.; Evaluation Of Ultracision In Lung Metastatic Surgery; Ann Thorac Surg. Oct. 2000; 70 (4): 1181-4; Department of Surgery I, General Surgery, Surgical Oncology and Thoracic Surgery, and Institute of Pathology, University of Leipzig, Germany. eichu@medizin.uni-leipzig.de.

*Enable Medical Introduces Second Generation Bipolar Scissors*; Health Industry Today, pNA; Dec. 1998.

Ercoli, A. et al.; *Radiofrequency Bipolar Coagulation For Radical Hysterectomy: Technique, Feasibility And Complications*; Int J Gynecol Cancer. Mar.-Apr. 2003; 13 (2): 187-91;Department of Obstetrics and Gynecology, Catholic University, Rome, Italy.

*Everest Medical Announces Introduction Of 3mm Bipolar Forceps*; PR Newswire, p. 1002MNW021; Oct. 2, 1996.

*Everest Medical Discusses Patent Status; Forecasts $1 Million Revenue First Quarter; Introduces Next Generation Bipolar Scissors*; PR Newswire, pN/A; Mar. 31, 1994.

*Everest Medical Introduces New Quadripolar (TM) Cutting Forceps At The Global Congress Of Gynecologic Endoscopy Meeting*; PR Newswire p. 8927; Nov. 8, 1999.

*Everest Medical Releases Bicoag (TM) For Use In Treating Bleeding Ulcers*; News Release, p. 1; May 9, 1990.

*Everest Medical Reports Record First Quarter Results; Introduces Next Generation Bipolar Scissors*; PR Newswire, pN/A; Apr. 19, 1994.

Forestier D. et al.; *Do Bipolar Scissors Increase Postoperative Adhesions? An Experimental Double-Blind Randomized Trial*; Ann Chir. Nov. 2002; 127 (9): 680-4; Service de chirurgie generale et digestive, Hotel-Dieu, boulevard Leon-Malfreyt, 63058 Clermont-Ferrand, France.

Gerasin VA et al.; *Endoscopic Electrosurgery Of The Trachea And Bronchi*; Grudn Khir. Sep.-Oct. 1988; (5): 50-3.

Gyr, T. et al.; *Minimal Invasive Laparoscopic Hysterectomy With Ultrasonic Scalpel*; Am J Surg. Jun. 2001; 181 (6): 516-9; Department of Obstetrics and Gynecology, Regional Hospital, Lugano, Switzerland.

Harrell, AG et al.; *Energy Sources In Laparoscopy*; Semin Laparosc Surg. Sep. 2004; 11 (3): 201-9; Carolinas Laparoscopic and Advanced Surgery Program, Carolinas Medical Center, Charlotte, NC 28203, USA.

Hayashi A. et al.; *Experimental And Clinical Evaluation Of The Harmonic Scalpel In Thoracic Surgery*; Kurume Med J. 1999; 46 (1): 25-9; Department of Surgery, Kurume University School of Medicine, Japan.

Hefni, MA et al.; *Safety And Efficacy Of Using The Ligasure Vessel Sealing System For Securing The Pedicles In Vaginal Hysterectomy: Randomised Controlled Trial*; BJOG. Mar. 2005; 112 (3): 329-33; Department of Gynecology, Benenden Hospital, Kent TN17 7AX, UK.

Heniford BT et al.; *Initial Results With An Electrothermal Bipolar Vessel Sealer*; Surg Endosc. Aug. 2001; 15 (8): 799-801. Epub May 14, 2001; Carolinas Laparoscopic and Advanced Surgery Program, Department of General Surgery, Carolinas Medical Center, 1000 Blythe Boulevard, MEB # 601, Charlotte, NC, USA.

Kamat, AA et al.; Superiority Of Electrocautery Over The Suture Method For Achieving Cervical Cone Bed Hemostasis; Obstet Gynecol. Oct. 2003; 102 (4): 726-30; Department of Obstetrics and Gynecology, Baylor College of Medicine, Houston, Texas 77030, USA. akamat@bcm.tmc.edu.

Kato, K. et al.; *A Computer Based, Temperature Controlled Bipolar Electrocoagulation System*; Eur J Obstet Gynecol Reprod Biol. Sep. 1996; 68 (1-2): 119-22; Department of Obstetrics and Gynecology, University of Essen, Germany.

Kennedy, JS et al.; *High-Burst-Strength, Feedback-Controlled Bipolar Vessel Sealing*; Surg Endosc. Jun. 1998; 12 (6): 876-8; Valleylab, Inc., 5920 Longbow Drive, Boulder, CO 80301, USA.

Kim, Byungkyu et al.; *Design And Fabrication Of A Locomotive Mechanism For Capsule-Type Endoscopes Using Shape Memory Alloys (Smas)*; IEEE/ASME Transactions on Mechatronics, vol. 10, No. 1, p. 77-86; Feb. 2005; USA.

Koch, C. et al.; Determination Of Temperature Elevation In Tissue During The Application Of The Harmonic Scalpel; Ultrasound Med Biol. Feb. 2003; 29 (2): 301-9; Ultrasonics Section, Physikalisch-Technische Bundesanstalt Braunschweig, B raunschweig, Germany. christian.koch@ptb.de.

Kohler C. et al.; *Laparoscopic Coagulation Of The Uterine Blood Supply In Laparoscopic-Assisted Vaginal Hysterectomy Is Associated With Less Blood Loss*; Eur J Gynaecol Oncol. 2004; 25 (4): 453-6; Department of Gynecology, Friedrich Schiller University, Jena, Germany.

Kung, RC et al; A New Bipolar System For Performing Operative Hysetroscopy In Normal Saline; Aug. 1999; 6 (3): 331-6J Am Assoc Gynecol Laparosc. http://www.ncbi.nlm.nih.gov/entrez/query.fcgi?cmd=Retrieve&db=pubmed&dopt=Abstract&list_uids=10459037&query_hl=1.

Kwok, A. et al.; *Comparison Of Tissue Injury Between Laparosonic Coagulating Shears And Electrosurgical Scissors In The Sheep Model*; J Am Assoc Gynecol Laparosc. Aug. 2001; 8 (3): 378-84; Department of Endosurgery, Women's Institute, University of Sydney, Australia.

Landman J. et al.; *Evaluation Of A Vessel Sealing System, Bipolar Electrosurgery, Harmonic Scalpel, Titanium Clips, Endoscopic Gastrointestinal Anastomosis Vascular Staples And Sutures For Arter Ial and Venous Ligation In A Porcine Model*; J Urol. Feb. 2003; 169 (2): 697-700; Department of Surgery (Division of Urology), Washington University School of Medicine, St. Louis, Missouri, USA.

Lantis, JC II et al.; *Comparison Of Coagulation Modalities In Surgery*; J Laparoendosc Adv Surg Tech A. Dec. 1998; 8 (6): 381-94; Surgical Research Laboratory, New England Medical Center, Boston, Massachusetts, USA.

*Laparoscopic Lasers Vs. Electrosurgery: Debated Technology Choices*; The BBI Newsletter, v.14, n. 6, pN/A; Jun. 6, 1991.

Levy, Barbara et al.; Update On Hysterectomy: New Technology AndTechniques;http://www.obgmanagement.com/supplements/pdf/hysterectomy.pdf; A supplement to OBG Management, Feb. 2003.

Levy, Barbara; *Use Of A New Vessel Lilgation Device During Vaginal Hysterectomy*; As presented at FIGO 2000, Washington, D.C.; University of Washington School of Medicine; Federal Way, Washington, USA; © 2000 Valleylab.

Lin, J. et al.; Application Of Ultrasonic Scalpel In Gynecologic Operative Laparoscopy; Chin Med J (Engl.) Dec. 2001; 114 (12): 1283-5; Department of Gynecology, Women's Hospital, Medical School of Zhejiang University, Hangzhou 310006, China. Zuying@mail.hz.zj.cn.

Lyons, TL et al.; An Innovative Bipolar Instrument For Laparoscopic Surgery; JSLS. Jan.-Mar. 2005; 9 (1): 39-41; Center for Women's Care & Reproductive Surgery, Atlanta, Georgia, USA cwcrs@mindspring.com.

*Market And Technology Updates: Bipolar Endoscopic Device*; The BBI Newsletter, v.13, n. 1, pN/A; Jan. 24, 1990.

Matsumura Y. et al.; *New Surgical Technique Of Pulmonary Segmentectomy By Ultrasonic Scalpel And Absorbable Sealing Materials*; Kyobu Geka. Jan. 2004; 57 (1): 31-7; Department of Thoracic Surgery, Institute of Development, Aging and Cancer, Tohoku University, Sendai, Japan.

Mundt, C. et al.; *Advanced Sensor Systems For Improved Labor And Fetal Monitoring*; ISA TECH/EXPO Technology Update Conference Proceedings v. 2 n. 2 1998, p. 79-89; 1998.

Nikolov, N. et al.; *Remote Controllable Vessel Occlusion Device*; Med Biol Eng Comput. Jan. 1978; 16 (1): 116-7.

U.S. Patent Issued For Novare Surgical Systems Cygnet (R) Surgical Clamp; Novare Signs Multi-Year Supply Agreement With Boston Scientific; PR Newswire, pNA; Sep. 2, 2003.

Ou, CS et al.; Total Laparoscopic Hysterectomy Using Multifunction Grasping, Coagulating, And Cutting Forceps; J Laparoendosc Adv Surg Tech A. Apr. 2004; 14 (2): 67-71; Department of Research and Development, Northwest Hospital and University of Washington School of Medicine, Seattle, Washington 98155, USA. cou@nwhsea.org.

Pavlov, IUV et al.; *Ultrasonic Technologies In Diagnosis And Treatment Of Patients With Surgical Diseases Of Lungs And Pleura*; Khirurgiia (Mosk). 2003; (8): 30-4.

Petrakis, IE et al.; Use of the Ligasure Vessel Sealer In Total Abdominal Hysterectomy; Int J Gynaecol Obstet. Jun. 2005; 89 (3): 303-4. Epub Mar. 2, 2005.; Department of General Surgery, University General Hospital of Heraklion, University of Crete, Heraklion, Crete, Greece. petrakis@post.com.

*Quadripolar Cutting Forceps Introduced By Everest Medical*; Health Industry Today, v. 63, n. 1, pNA; Jan. 2000.

*Radiofrequency Energy Proven Effective Against Leading Cause Of Obstructive Sleep Apnea*; Business Wire, p. 09140175; Sep. 14, 1998.

Raestrup, H. et al.; *Dissection Technique—Is Ultrasound The Best Method?*; Kongressbd Dtsch Ges Chir Kongr. 2001; 118: 69-70; Universitatsklinik Fur Allgemeine Chirurgie, Hoppe-Seyler-Strasse 3, 72076 Tubingen.

Robinson JL et al.; *Bipolar Diathermy*; Can J Surg. Sep. 1974; 17 (5): 287-91.

Srisombut, C. et al.; *Laparoscopic Hysterectomy Using Laparosonic Coagulating Shears: Experience Of 15 Cases*; J Med Assoc Thai. Aug. 2000; 83 (8): 915-20; Department of Obstetrics and Gynecology, Faculty of Medicine, Ramathibodi Hospital, Mahidol University, Bangkok, Thailand.

Stanojevic, D. et al.; *An Ultrasonic Scalpel For Laparoscopic Gynecologic Surgery*; Srp Arh Celok Lek. May-Jun. 1998; 126 (5-6): 214-6; Narodni Front Department of Gynecology and Obstetrics, Dr. Dragisha Mishovitsh Medical Centre, Belgrade.

Sugi, K. et al.; *Use Of The Bipolar Vessel Sealing System In Lung Resection*; Kyobu Geka. Jul. 2003; 56 (7): 551-4; Department of Clinical Research, National Sanyo Hospital, Ube, Japan.

Tajiri M. et al.; *Evaluation Of An Ultrasonic Cutting And Coagulating System (Harmonic Scalpel) For Performing A Segmental And Wedge Resection Of The Lung* ; Kyobu Geka. Dec. 1998; 51 (13): 1116-9; Department of Surgery, Kan to Rosai Hospital, Kawasaki, Japan.

Tamussino, K. et al.; Electrosurgical Bipolar Vessel Sealing For Radical Abdominal Hysterectomy; Gynecol Oncol. Feb. 2005; 96 (2): 320-2;Department of Obstetrics and Gynecology, Medical University of Graz, Auenbruggerplatz 14, A-8036 Graz, Austria. Karl.tamussino@meduni-graz.at.

The Gynecare Versapoint; http://www.jnjgateway.com/home.jhtml?loc=USENG&page=viewContent&contentId=edea000100001747&parentId=fc0de00100000334; All contents copyright © Johnson & Johnson Gateway, LLC 2000-2005.

Timor-Tritsch IE et al.; Transvaginal Ultrasound-Assisted Gynecologic Surgery: Evaluation Of A New Device To Improve Safety Of Intrauterine Surgery; Am J Obstet Gynecol. Oct. 2003; 189 (4): 1074-9; Department of Obstetrics and Gynecology, New York University School of Medicine, NY 10016, USA. ilan.timor@med.nyu.edu.

Tucker, R.D. et al.; *Capacitive Coupled Stray Currents During Laparoscopic And Endoscopic Electrosurgical Procedures*; Biomedical Instrumentation & Technology vol. 26, No. 4 p. 303-11; Jul.-Aug. 1992; USA.

Tucker, RD et al.; *Bipolar Electrosurgical Sphincterotomy*; Gastrointest Endosc. Mar.-Apr. 1992; 38 (2): 113-7; Department of Pathology, University of Iowa Hospitals Clinics, Iowa City 52242.

*Valley Forge Scientific Corp.—Company Report*; Investext, p. 1-1; Jan. 27, 1993.

Valleylab Products—Electrosurgical Forceps: The Surgeon's Choice For Quality And Precision; http://www.valleylab.com/product/es/accessories/forceps_over.html; © 2005 valleylab.

Weyl, BP; *How To Increase The Proportion Of Vaginal Hysterectomies—Bipolar Coagulation*; Am J Obstet Gynecol. Sep. 1999; 181 (3): 768.

Wilson, Fred; *Cool Tool, Hot New Application: Radiofrequency Energy Removes Head, Neck Tumors. (Dermatologic Surgery)*; Dermatology Times, v. 24, n. 8, p. 54; Aug. 2003.

Zhi, Xu-Ting et al.; *Management Of Gastroesophageal Reflux Disease: Medications, Surgery, Or Endoscopic Therapy? (Current Status and Trends)*; Journal of Long-Term Effects of Medical Implants v. 15 n. 4 2005. p. 375-388; 2005.

*Gyrus Medical: LP Scissors*; [online] date of publication not found; [retrieved on Oct. 20, 2005] from website: http://www.gyrusgroup.com/medical/products_item.asp?id=11.

Gyrus Medical: Micro/Macro-Jaw Forceps; [online] date of publication not found; [retrieved on Oct. 20, 2005] retrieved from website: http://www.gyrusgroup.com/medical/products_item.asp?id=13.

Gyrus Medical: Cutting Forceps; [online] date of publication not found; [retrieved on Oct. 20, 2005] retrieved from website: http://www.gyrusgroup.com/medical/products_item.asp?id=7.

Gyrus Medical: Lyons TM Dissecting Forceps; [online] date of publication not found; [retrieved on Oct. 20, 2005] retrieved from website: http://www.gyrusgroup.com/medical/products_item.asp?id=8.

Gyrus Medical: Seal TM Open Forceps; [online] date of publication not found; [retrieved on Oct. 20, 2005] retrieved from website: http://www.gyrusgroup.com/medical/products_item.asp?id=15.

Valleylab Products—Ligasure TM Vessel Sealing System; [online] date of publication not found; [retreived on Oct. 20, 2005] retrieved from website: http://www.valleylab.com/product/vessel_seal/index.html © 2005 valleylab.

\* cited by examiner

APPARATUS FOR TISSUE CAUTERIZATION

CROSS REFERENCE TO RELATED APPLICATIONS

The application claims priority to U.S. Provisional Patent Application Ser. No. 60/725,720, filed Oct. 11, 2005, and Ser. No. 60/680,937, filed May 12, 2005, the entirety of each of which is incorporated herein by this reference thereto.

BACKGROUND OF THE INVENTION

1. Field of the Invention

The invention relates generally to tissue cauterization. More particularly, the invention relates to an improved electrode for tissue cauterization.

2. Description of the Background Art

Tissue and organ removal are required in a number of surgical procedures for a number of purposes. A major concern in all tissue removal procedures is hemostasis, ie. cessation of bleeding. All blood vessels supplying an organ or a tissue segment to be removed have to be sealed, either by suturing or cauterization, to inhibit bleeding when the tissue is removed. For example, when the uterus is removed in a hysterectomy, bleeding must be inhibited in the cervical neck which is resected, as well as along the vessels which supply blood to the uterus along its sides. Similarly, blood vessels within the liver must be individually sealed when a portion of the liver is resected in connection with removal of a tumor or for other purposes. The liver is a highly vascularized organ and sealing of the blood vessels is quite time consuming. Achieving hemostasis is necessary in both open surgical procedures and in minimally invasive surgical procedures. In the latter case, however, because of the limited access through cannula and other small passages, sealing of blood vessels can be even more time consuming and problematic.

Achieving hemostasis is particularly important in laparoscopic and other limited access procedures where the organ or other tissue must be morcellated prior to removal. Most organs are too large to be removed intact through a cannula or other limited access passage, thus requiring that the tissue be morcellated, e.g. cut, ground, or otherwise broken into smaller pieces, prior to removal. It will be appreciated that morcellation of vascularized tissue can be very problematic.

For these reasons, it would be desirable to provide improved methods, systems, and apparatus, for achieving hemostasis in connection with organ and tissue removal procedures. In particular, it would be desirable to provide methods and systems which permit a surgeon to achieve hemostasis in a time-efficient manner, using readily available surgical equipment e.g. radio frequency power supplies as discussed below, while reducing risk and trauma to the patient. It would be further desirable if the methods and systems are applicable to a wide variety of tissue removal procedures, including at least hysterectomies, liver tissue resection, cholecystectomies, prostate removal, lung resection, and the like. It would be still further desirable if the methods could provide for complete or substantially complete coagulation and hemostasis of an entire volume of tissue to be removed to facilitate such procedures as a subsequent morcellation. The ability to, for example, morcelate tissue while minimizing bleeding will be of substantial benefit to the performance of laparoscopic and other minimally invasive procedures, as well as other surgical procedures.

The use of radio frequency (RF) energy to necrose body organs or portions thereof is known. U.S. Pat. No. 4,979,948 describes a balloon electrode which is inflated in the interior of a uterus and used to apply RF energy to necrose the endothelial lining of the uterus. U.S. Pat. No. 3,845,771 describes a glove having flexible electrodes on the thumb and middle finger. The glove is intended for conducting RF current to conventional forceps, scalpels, etc. U.S. Pat. No. 4,972,846 describes electrode patch pairs useful as defibrillator leads which are engaged directly on the epicardium. U.S. Pat. Nos. 5,178,618 and 5,078,736 describe stents which can be energized to apply RF energy on the interior of a body lumen. Lorentzen et al. (1996) Min. Ivas. Ther. Allied Technol. 5:511-516 describes a loop electrode that can be rotated within tissue to excuse a tissue volume.

U.S. Pat. No. 6,203,541 discloses an automatic circuit that controls a surgical instrument, having a pair of bipolar electrodes. The circuit comprises a means for measuring the current between the pair of electrodes, an impedance detection circuit that is in electrical communication with the current measuring means, a comparator that has an electrical communication with the impedance detection circuit, and a controller that is electrically connected to the comparator. The impedance detection circuit calculates the impedance between the electrodes based on the measured currents and generates a first signal indicative of the calculated impedance. The comparator processes the first signal and generates an activation signal if the calculated impedance falls within a predetermined range of impedance values and generates a deactivation signal if the calculation impedance exceeds a deactivation threshold. The controller receives the activation and deactivation signals and transmits the first control signal to a radio frequency energy output stage to activate the electrodes in response to the activation signal and transmits the second control signal to the radio frequency output stage to deactivate the electrodes in response to the deactivation signal.

U.S. Pat. No. 6,398,779 teaches a method for electrosurgically sealing a tissue that concludes the steps of applying an initial pulse of RF energy to the tissue, the pulse having characteristics selected so as not to heat the tissue appreciably; measuring the value of the impedance of the tissue and response to the applied pulse; and in accordance with the measured impedance value, determining an initial set of pulse parameters for use during a first RF energy pulse as applied to the tissue. The invention teaches varying the pulse parameters of individual ones of subsequent RF energy pulses in accordance with at least one characteristic of an electrical transient that occurs during subsequent RF energy pulses. The method terminates the generation of subsequent RF energy pulses upon a determination that the electrical transient is absent or that a minimum output voltage has been reached.

U.S. Pat. No. 5,443,463 teaches a coagulating forceps for selectively coagulating blood vessels or tissue containing blood vessels. The method taught involves the placement of the blood vessels or tissue containing blood vessels between the prongs of the forceps, with the jaws of the forceps containing a plurality of electrodes which are energized by radio frequency power. A plurality of sensors are associated with the electrodes, and in contact with the vessels or tissue, to measure the temperature rise of the tissue or blood vessels and to provide a feedback to the radio frequency power to control the heating to perform coagulation of vessels or tissue. The invention also teaches that the upper prong of the device may be split into two parts with the cutting blade between the two upper parts to provide for cutting of the coagulated vessels subsequent to the coagulation.

SUMMARY OF THE INVENTION

The invention provides methods, systems, and apparatus which facilitate tissue cauterization in connection with such procedures as tissue resection and removal from patients undergoing a wide variety of procedures. The procedures may involve removal of an entire organ, e.g. hysterectomies, cholecystectomies, prostate removal, lung resection, and the like. Alternatively, the methods may involve removal of a portion of an organ or other tissue, such as tumor removal, often from highly vascularized organs, such as the liver, lung, or the like. The methods generally involve two steps, where the tissue is first necrosed or cauterized in whole or in part using radio frequency energy. In particular, the cauterization is effected at least along a desired resection plane within the tissue. The tissue is then resected along said plane(s). Advantageously, it has been found that resection within the necrosed or cauterized tissue substantially minimizes, and in some cases eliminates, the bleeding caused by the tissue resection. Preferably, the tissue cauterization is effected over a target volume of tissue, typically an entire organ or a portion thereof, e.g. the uterus, the lobe of a liver, a lung section, the prostate, or the like. By effecting substantially complete cauterization of a target tissue volume, the bleeding capacity of that tissue is reduced or eliminated, thus facilitating subsequent morcellization and tissue removal. Thus, organ and tissue removal is greatly facilitated with a substantial reduction in bleeding and the time needed for the surgical procedure.

In a first specific aspect, methods according to the invention comprise engaging at least a first electrode structure and a second electrode structure against spaced-apart surfaces of a tissue mass, typically against opposed surfaces of the tissue mass. The first and second electrode structures may have generally similar geometries to contact tissue in a symmetric fashion. Alternatively, the electrode structures may have dissimilar geometries, e.g. one of the electrode structures may be configured as a probe for insertion into a natural body orifice with the other electrode structure being configured for engagement against an exterior tissue surface spaced-apart from said orifice. In some instances, more than two electrode structures may be employed, but at least two electrode structures (or separate regions of a single structure) are energized with opposite polarity to provide for application of the radio frequency energy to the tissue. In some other instances, the electrode structures may be different regions formed as part of a single support structure, e.g. a single elastic tube or shell which may be placed over an organ or other tissue mass and which has two or more electrode surfaces formed thereon. The different electrode surfaces are, of course, isolated from each other when they are intended to apply high frequency energy of opposite polarities. It is equally important for the electrodes not be in contact if they are of like polarity as well. In still other instances, a single electrode structure may have a plurality of electrically conductive or active regions, where the electrically conductive regions may be energized with the same or an opposite polarity. In other instances, electrode structures may be provided with tissue-penetrating elements to enhance electrode-tissue contact and increase the total available area of the electrically active region(s) on the electrode structure to deliver high frequency energy to the tissue. The use of such tissue-penetrating elements may be in addition to or in place of the use of conformable or rigid surface electrodes. In all instances, the electrode structures, or electrically active regions thereof, are configured to engage a substantially continuous segment or portion of the tissue surface having a minimum area as set forth below. When tissue-penetrating elements are used, they typically are dispersed in a general uniform matter over the electrically active area of the electrode structure.

High frequency (usually radio frequency) power is applied to the tissue mass through the electrically active regions(s) of the electrode structures, and the power is applied for a time and in an amount sufficient to cauterize or necrose tissue between said electrodes, preferably at least along a desired resection plane. Often, a volume of the tissue is resected by morcellating, e.g. grinding, comminuting, cutting into small pieces, or the like. Such morcellation is greatly facilitated by necrosis of the target tissue volume. By necrosed, it is meant that the cells of the tissue have been killed and that bleeding of the tissue, upon subsequent resection, has been substantially inhibited. The tissue are usually resected along a plane within the necrosed tissue mass, with minimal bleeding as described above.

The electrically active regions of the electrode structures have an area of at least 1 $cm^2$, more usually at least 2 $cm^2$, often having areas of 5 $cm^2$ or larger, more often having areas of 10 $cm^2$ or larger, still more often having areas of 50 $cm^2$ or larger. The electrodes may have a wide variety of characteristics, may generally be rigid, flexible, elastic, malleable, conformable, or the like. Preferably, the electrodes flexible to facilitate engagement of the electrode against, and conformance to, a tissue surface. In at least some instances, it is desirable to provide flexible, elastic electrodes which may be conformed about the outer periphery of a tissue or organ surface, where the elastic nature of the electrode assures firm engagement and electrode contact. In other instances, however, the electrodes may be specifically configured to have a desired geometry for engaging a particular tissue surface.

The high frequency energy applied to the organ or tissue is generally provided at radio frequency typically, but not limited to the range from 100 kHz to 10 MHz, usually from 200 kHz to 750 kHz. The power levels depend on the surface area and volume of tissue being treated, but generally fall within the range from 10 W to 500 W, usually from 25 W to 250 W, more usually from 50 W to 200 W. Power is usually applied at a level of from 1 $W/cm^2$ to 500 $W/cm^2$, more usually from 10 $W/cm^2$ to 100 $W/cm^2$. The power is applied for a time sufficient to raise the tissue temperature in the tissue mass being treated to above a threshold level required for cauterization or necrosis, usually being above at least 60° C., frequently being above 70° C., and often above 80° C., or higher. The application of energy should be limited, however, so that adjacent tissue is not significantly heated or otherwise damaged. The use of opposed, bipolar electrodes is particularly advantageous in this regard because it concentrates the energy flux between the electrodes and limits the effect on adjacent tissue which are not confined within the opposed electrodes. The resulting necrosed tissue may comprise substantially the entire organ being treated, or in other cases may comprise a more narrow region, e.g. a planar region.

In another aspect, the invention comprises systems including at least a plurality of electrodes, and a power supply that is connectable to the electrodes for applying, for example, bipolar, high frequency power therebetween. The electrodes may be configured generally as described above, and are usually carried by an electrosurgical probe to facilitate deployment. The probe may have a wide variety of configurations, but usually comprises at least a shaft and a handle for manipulating the shaft. The electrodes are mounted at a distal end of the shaft and are usually manipulable from the proximal end of the shaft so that they may be opened and closed relative to each other to engage and capture an organ or other tissue mass therebetween. The electrodes may have any of the properties described above, and may in particular comprise metallic or metallized mesh which can elastically engage and conform to tissue surfaces. The electrosurgical probes may be used in a conventional bipolar manner, i.e. where each electrode is powered at an opposite polarity. Alternatively, the electrode surfaces may be powered at the same polarity with another electrode or electrodes used for completing the high frequency circuit. Typically, the other electrode(s) are in the form of one or more probes which may be inserted into a natural body orifice or lumen or may be introduced into an organ or other tissue mass. The probe(s) may conform to a natural lumen and/or saline or other electrically conductive fluid may be introduced into the lumen to help establish the conductive path.

In a specific embodiment, an electrosurgical device may comprise a single conformable structure, such as an elastically or non-elastically expansible tubular member, e.g. an expansible tubular braid mesh. The electrodes are formed on a plurality of locations over the conformable support structure and are usually isolated from each other, e.g. either by applying insulation or by relying on the inherently non-conductive nature of the conformable support structure.

DESCRIPTION OF THE SPECIFIC EMBODIMENTS

Figure 1:
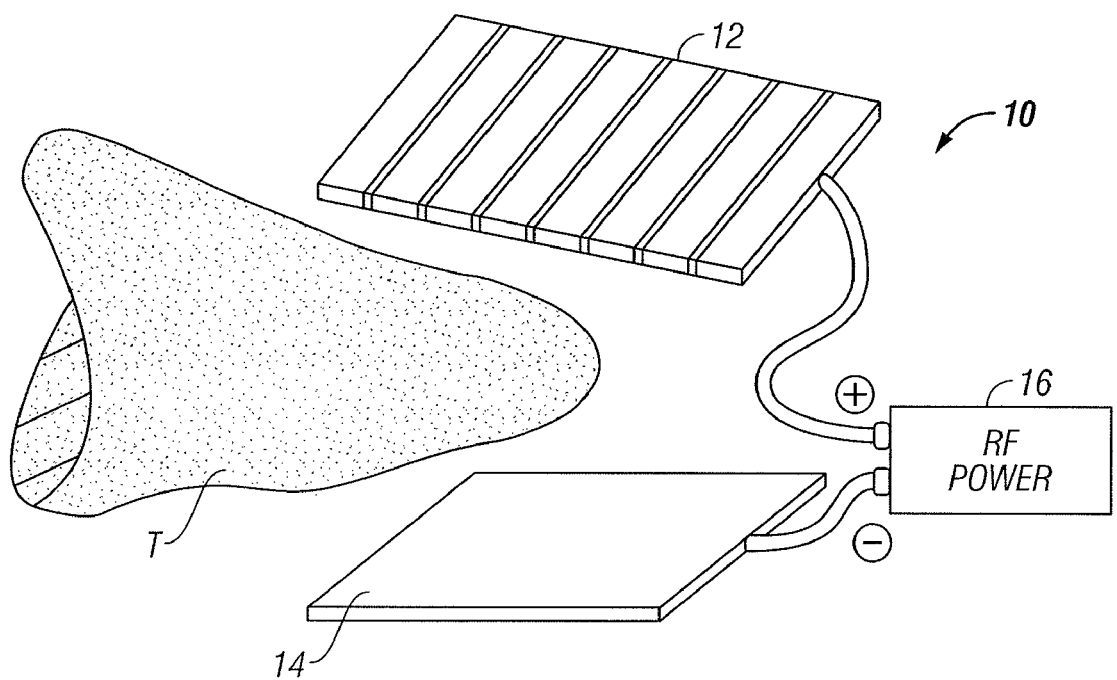
FIG. 1 is a conceptual illustration of the system and method of the invention employing a plurality of rigid, plate electrodes.

The methods, systems, and apparatus of the invention are useful for treating a variety of organs, portions of organs, or other solid tissue regions in a patient. The organ or other tissue mass have spaced-apart tissue surfaces, usually opposed tissue surfaces, which are accessible to electrode structures and which permit the application of radio frequency power between said surfaces. The tissue surfaces may be readily accessible or may require pre-treatment to gain access, e.g. blunt dissection, resection of small tissues or blood vessels using conventional surgical techniques, or the like. Organs which may be treated by the invention include the uterus, liver, prostate, kidney, bowel, pancreas, lung, breast, muscle, and the like.

The organs and other tissue are treated with bipolar radio frequency power directed at target tissue regions which are defined by spaced-apart placement of the electrode structures. The radio frequency power may be supplied by conventional general purpose electrosurgical power supplies operated at any accepted frequency, typically in the ranges set forth above. Power supplies may employ conventional sinusoidal or non-sinusoidal wave forms and may operate with fixed or controlled power levels, where the voltage, current, or both may be selected. Suitable power supplies are available from commercial suppliers, such as Valleylab, Aspen, and Bovie. In some instances, it will be desirable to use impedance matching transformers between the power supply and the electrodes to enhance the efficiency of energy delivery.

The electrodes may be configured in any manner suitable for engaging a tissue surface. Thus, the electrodes can be rigid, flexible, elastic, inelastic (non-distensible), planar, non-planar, or the like, and may optionally employ tissue-penetrating elements to enhance electrical contact between the electrode structure and the tissue, as well as to increase the electrode area. Preferred electrode configurations are either conformable so that they can be engaged against and conform to widely differing tissue surfaces (see, for example, U.S. patent application Ser. No. 11/371,988 (Attorney Docket No. ARGA0003), the entirety of which is incorporated herein by this reference thereto), or they are specifically configured to have a geometry intended to engage a particular organ or tissue geometry. In both instances, the electrode structures may further be provided with tissue-penetrating elements. Examples of each are discussed hereinafter.

One electrode configuration uses a metallized mesh which is both flexible and elastic. Such meshes are suitable for use on retractable electrodes, such as retractable electrodes useful for minimally invasive procedures. The meshes may be suspended on or between more rigid frame members, where the frame members may be themselves expanded or contracted to deploy the mesh electrodes. Such meshes are also useful for fabricating elastic tubes or shells which may be placed over an organ or tissue mass like a sock. In the case of such tubular electrodes, it often desirable to form two or more discrete electrode surfaces on a single mesh, where the electrode surfaces are isolated, usually by virtue of the material properties of the mesh itself, i.e. they are polymeric and non-conductive. The elastic meshes can be in the form of a braid or other woven structure, e.g. as described in U.S. Pat. Nos. 5,431,676; 5,234,425; and 4,018,230, the full disclosures of which are incorporated herein by reference. The use of radially expansible braid structures is desirable because the diameter of the tissue-receiving lumen therein can be controlled by axial elongation. That is, the braid can be expanded by shortening its length and contracted by extending its length. All such mesh and braid structures can be metallized by conventional electroless plating techniques. Suitable for metals for plating include gold, silver, copper, stainless steel, and combinations and alloys thereof. Suitable elastomeric mesh materials include a wide variety of elastomers. Suitable braided mesh materials include nylon and other generally non-distensible polymers.

All types of electrode structures may be configured to have a conductive surface and a non-conductive surface. This is usually accomplished by leaving one surface as an exposed metallic face, while the other surface of the electrode is covered or insulated. In the case of rigid electrodes, the insulation can be laminated, coated, or otherwise applied directly to the opposed surface. In the case of flexible and elastic electrodes, it is necessary that the insulating layer also be flexible so that it can be expanded and contracted together with the electrode without loss or removal. In some cases, it is desirable to employ a separate sheet of material which is expanded together with the electrode and which covers the face which is desired to be insulated.

Referring now to FIG. 1, a system 10 according to the invention comprises a first, compound electrode 12, a second electrode 14, and a radio frequency power supply 16. The first electrode comprises a plurality of rigid plates that are independently connected to one pole of the power supply 16 and the second electrode is a rigid plate connected to the opposite pole. In other embodiments, the second electrode could be non-rigid and could represent multiple electrodes as well. In fact, multiple return electrodes are preferable in certain cases. The electrodes 12 and 14 can be engaged against a tissue mass T to engage opposed surfaces thereof. Radio frequency power is then selectively applied to the tissue through any combination of the plurality of rigid plates which form electrode 12 (as discussed in greater detail below) to cauterize the mass of tissue which is captured between the electrodes 12 and 14 completely. After the tissue is cauterized, it may be resected along a line within the cauterized region of tissue. Advantageously, resection within the cauterized tissue minimizes bleeding and simplifies hemostasis.

For use in cauterizing the tissue of, for example, the uterus, conformable electrodes and may be placed over opposed exterior surfaces of the uterus. Rather than applying high frequency energy of opposite polarities, as generally described above, the electrodes may be powered at a common polarity by a power supply. A probe may be inserted into the uterine cavity and powered at the opposite polarity. In this way, the opposed tissue surfaces comprise the interior lining of the uterine cavity on the one hand and the exterior surface of the uterus on the other hand. In the case of the uterus, it is generally desirable to cauterize substantially the entire tissue mass, with the possible exception of the cervical neck. In the case of other body organs and tissue masses, however, it may be desirable to cauterize only a portion of the tissue. The high frequency energy can be directed to limited portions of the tissue by choosing the configurations of the electrodes.

Preferably, the electrodes comprise a plurality of different electrically conductive regions, where the regions may be electrically isolated from each other or may be electrically coupled to each other. Single electrode structures may include three, four, five and as many as ten or more discrete electrically conductive regions thereon. Such electrically conductive regions are usually defined by electrically insulating regions or structure therebetween. When it is desired that two or more of the electrically conductive regions be electrically coupled, small electrical connections can be provided to bridge the insulation between the regions. Usually, at least some of the isolated, electrically conductive regions on the electrode structures are powered at opposite polarities, and in some instances the methods of the invention can be performed using only a single electrode structure having multiple electrically conductive regions thereon. Alternatively, isolated, electrically conductive regions on a single electrode structure may be powered at the same polarity, where a primary purpose of the different regions is to control or configure the high energy electrical flux being delivered into the tissue mass. For example, it may be desirable to deliver high frequency electrical energy into spaced-apart regions of a tissue mass without cauterizing other areas in between or adjacent to the region to be cauterized. In such cases, the electrode structures can be configured by appropriate placement of the electrically conductive regions.

Figure 2:
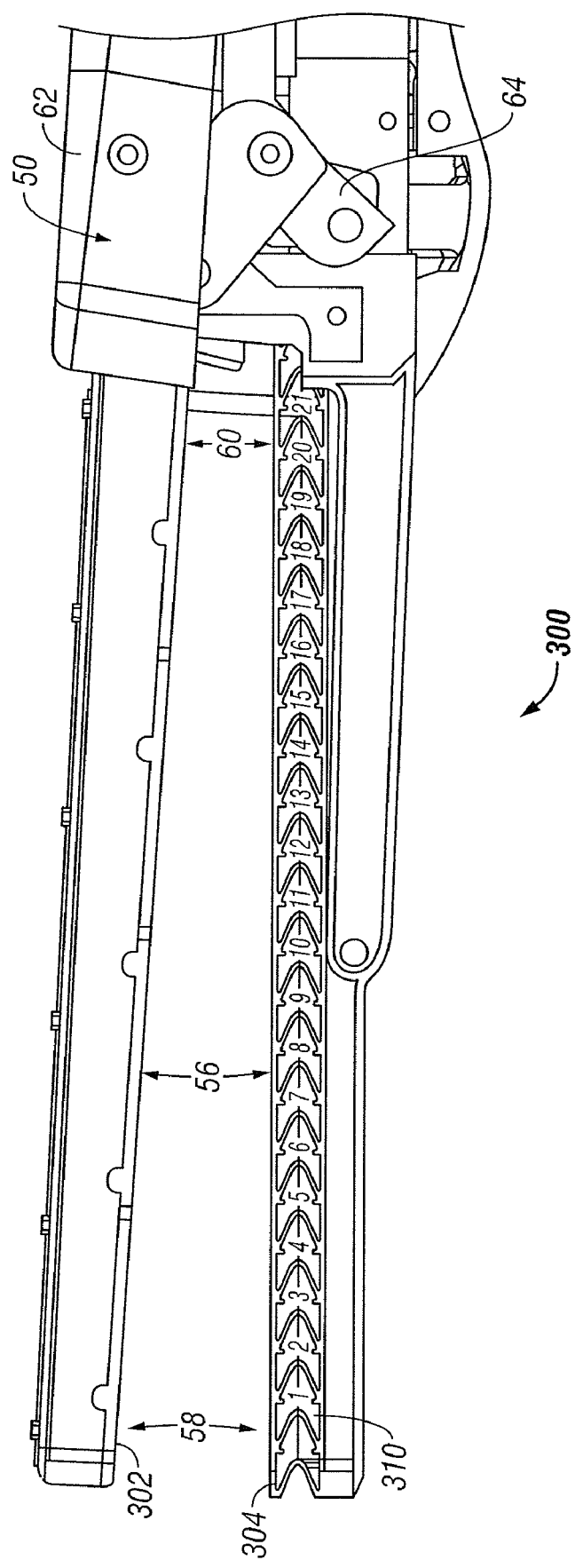
FIG. 2 illustrates an electrosurgical probe comprising an electrode structure configuration where each electrode structure comprises a plurality of electrically isolated active surfaces.

FIG. 2 illustrates a system 300 that comprises a pair of electrode structures 302 and 304. At least one of the electrode structures 304 comprises a plurality of individual electrically conductive strips 31 0 which are spaced apart such that they are electrically isolated from each other. In other embodiments, the conductive strips may be separated by an electrically insulating material. The electrically conductive strips 310 may be selectively powered at different polarities in virtually any pattern. Often, it is desirable to energize the strips so that adjacent strips have opposite polarities. Those skilled in the art will appreciate that the electrodes may be discrete or that they may be formed by such techniques as screening, electrodeposition, and the like.

To this point in the description, the electrically conducted surfaces of the electrode structures have generally comprised rigid or conformable components having continuous surface geometries, i.e. surface geometries which are selected to create an uninterrupted interface with the tissue surface against which they are engaged. In some instances, it may be desirable to provide additional structure or components on the electrode structures to enhance or increase the effective electrical contact area between the electrode structure and the tissue surface. In particular, it is often desirable to provide tissue-penetrating elements on the electrode structures to both enhance electrical contact, tie reduce electrical impedance between the electrode and the tissue and, more importantly, to increase the total surface contact area between the electrode and the tissue. The tissue-penetrating elements may be needles, pins, protrusions, channels, or the like, but are usually pins having sharpened distal tips so that they can penetrate through the tissue surface and into the underlying tissue mass. The pins may have depths in the rage from 1 mm to 5 cm, usually being from 3 mm to 1 cm. The diameters of the pins may be from 0.1 mm to 5 mm, usually being from 0.5 mm to 3 mm. Usually, the pins are evenly distributed over the tissue-contact area of an electrode structure, with a pin density in the range from 0.1 pin/cm$^2$ to 10 pin/cm$^2$, usually from 0.5 pin/cm$^2$ to 5 pin/cm$^2$. Usually, the pins or other tissue-penetrating elements are provided in addition to an electrically conductive conformable or rigid electrode surface, but in some instances the pins may provide the total electrically conductive or active area of an electrode structure.

A system comprising a pair plurality of electrode structures can include electrically conductive strips separated, for example, by insulating rods. In addition, however, tissue-penetrating pins can be disposed along each of the electrically conductive strips. It is appreciated that a plurality of pins are disposed along the length of each strip. The electrode structures are generally of a curved configuration so that they may be placed over a tubular body structure or tissue mass. It is appreciated, however, that the strips may be formed from conformable meshes which permit the electrode structures to be flattened out or to assume a wide variety of other configurations. Additionally, the insulating structures may also be formed from a flexible or conformable material, permitting further reconfiguration of the electrode structures.

The electrically conductive strips may be energized in an alternating polarity configuration. Most simply, adjacent strips are connected to opposite polls on a single power supply. It is a simple matter, however, to rearrange the electrical connections to power the strips in virtually any pattern. Moreover, it is also possible to isolate different regions of each strip electrically e.g. nos. 1 and 2 to permit powering those regions at different polarities.

Using the system 300, a variety of different tissue cauterization patterns can be achieved by selective energization of different ones of the electrode surfaces or regions. By selectively energizing two adjacent electrode surfaces in a bipolar fashion, while leaving all other surfaces non-energized, a limited tissue region is cauterized. In contrast, by energizing other electrode surfaces e.g. nos. 4, 5, 6, and 7, a much larger region is cauterized. Slightly different patterns are achieved depending on the precise pattern of electrode surface polarity. The electrode surfaces can be energized in an alternating pattern of polarity (+, −, +, −) to produce a tissue cauterization pattern. Patterns of (+, +, −, −); (+, −, −, +); (−, +, +, −) etc., could also be used to produce somewhat different patterns of cauterizedtissue.

FIG. 2 illustrates an electrosurgical probe 50 that includes a pair of jaws 56 having a distal end 58 and a proximal end 60. Alternatively, this probe may comprise a shaft that is typically a cylinder sized for introduction through a conventional cannula of the type used in minimally invasive surgery. Thus, the shaft typically has a diameter in the range from 5 mm to 15 mm, usually being nominally 5 mm, 10 mm, or 12 mm, to be consistent with conventional cannulas. The length of the shaft typically in the range from 10 cm to 30 cm, with the particular range depending on the intended procedure.

The electrosurgical probe 50 includes a handle assembly 62 that is attached to the proximal end 60 of the jaws 56. The handle includes a lever assembly 64 which is connected to actuate the electrodes 304 after they are deployed. The handle also includes a coaxial connector for connecting the electrodes to an electrosurgical power supply, as described herein, although the electrodes may be powered by conventional power supplies as well. The electrosurgical probe 50 may be employed to cauterize and resect a portion of liver. For example, the probe may be introduced through a cannula, and the electrodes advanced and opened so that they can capture a portion of the liver L which is to be removed. After the electrodes are closed against opposed surfaces of the liver, the radio frequency energy may be applied, as described above. After the tissue is fully cauterized, it may be resected along any line within the necrosed tissue mass. Optionally, the electrosurgical probe may be used to cauterize a series of tissue masses adjacent each other to cauterize and resect a larger tissue mass than would be possible using only a single application of radio frequency energy.

In one embodiment, the electrodes may be used, for example, to cauterize and resect a uterus. The uterus comprises a main body having fallopian tubes extending from each side. In addition to the fallopian tubes, several large blood vessels extend generally from the midline of the uterus. The electrodes may be placed over the anterior and posterior surfaces of the uterus with the fallopian tubes remaining attached and extending outwardly from between the electrode structures. Depending upon the procedure, in some cases the fallopian tubes would be included in the sealed, cauterized, and dissected region and, in others, the choice may be not to seal and cauterize the fallopian tubes. This decision is based upon whether the ovaries are to be removed along with the uterus or not. Radio frequency power may then be applied to the uterus, typically at a power level in the range from 10 $W/cm^2$ to 100 $W/cm^2$ for a time in the range from 10 sec. to 20 min., until the body of the uterus is substantially completely necrosed. Because of the geometry of the electrodes the necrosed body of the uterus terminates along a line generally at the cervical end of the uterus, as well as along lines adjacent the fallopian tubes. The uterus may then be resected along lines within the cauterized tissue region but adjacent the cervix and fallopian tubes. Resection within the cauterized regions of the uterus substantially minimizes bleeding and facilitates hemostasis. The uterus may then be removed, either intact in the case of open surgical procedures. In the case of minimally invasive procedures, the uterus may optionally be morcellated (comminuted into small pieces) prior to removal.

In one embodiment of the invention, parallel electrodes are provided along the device, thus preventing positive-to-negative contact if opposing jaws and electrodes are brought into contact. In this embodiment, the oppositely charged electrodes that are mounted in the same jaws must be mounted in a non-conductive material to prevent shorting.

The jaws can be offset by a soft compressive material, such as a foam rubber, to prevent the electrodes from contacting, while assuring secure contact with all intermediate tissue. This embodiment of the invention can accommodate variable tissue thicknesses, which are expected to be likely over 5-10 cm of tissue.

To prevent local areas of high impedance from impacting the overall system impedance along the entire electrode, and thus potentially reducing the power output of the entire system as the voltage reaches its maximal capacity, multiple electrodes could be located physically in series. These electrodes may be powered simultaneously or in a repetitive sequential or other series. The electrodes may also be powered entirely independently of each other. In this manner, if one area that has already been well sealed and has thus reached high impedance value, it does not affect other regions in which the tissue is not yet sealed, and is thus at a lower impedance, i.e. impedance goes up as sealing occurs and this can limit power transmission. Each electrode or electron pair can have unique power and energy delivery profiles, based on the properties of the tissue in a specific electrode location/position.

As should be apparent from the disclosure herein, there is a benefit to using longer electrosurgery electrodes or other high-energy sealing impedance mechanisms to save operating time in a number of surgical procedures. For example, depending on the makeup of the tissue involved and its thickness along the length of tissue to be cauterized, geometry variations of both the electrosurgical jaws and power supply may be optimized to facilitate surgical removal of part or all of particular organs.

For example, the connective tissue or ligaments of the uterus are relatively thin and of relatively low impedance, ie. less than three Ohms in many cases before energy is delivered to the tissue, based on animal models. However, this impedance is not constant, both along the length of tissue being cauterized, and during the course of cauterization. Therefore, a power supply with a capacity of, for example, less than 100 volts is not adequate to seal and coagulate all tissue and blood vessels supporting the organ fully because it is often necessary to ramp up the voltage after initially applying power to cauterize the tissue to maintain power levels in light of increasing impedance as the sealing and cauterization process progresses. Further, for thicker tissue or organs, such as the liver, lungs, or bowel, or for longer segments of tissue, significantly higher voltages are likely to be required. For more delicate tissues or locations, high voltage power energy levels may not be safe. In addition, due to the higher impedance of some of these organs and tissues, the power supply must have sufficient cut-off for discontinuing power to the organ at the end of the sealing cycle. Thus, the power supply should automatically terminate current flow to the tissue once the power supply has determined the completion of the sealing cycle. Although manually discontinuing power delivery is an option, it is less desirable because it is subjective and it is less likely to include an accurate analysis of the condition of the tissue or organ. The automatic feedback system disclosed herein prevents excessive heating or burning of surrounding healthy tissues and organs, as well as minimizing tissue adhesion to the electrodes, while assuring adequate vessel sealing. Therefore, the power supply herein has multiple adjustable settings that the user can select based on the organ to be treated. A prior characterization of each organ determines preset voltage limits and curves, as well as final shutdown (endpoint) parameters based on time, impedance, voltage, current, temperature or energy data, or some combination of these for each specific organ. Therefore, processes that optimize safety and efficacy for the specific procedure are used. Based on the degree of vascularity and size of the blood vessels present, various tissues and organs may require different settings as well.

Another embodiment of the invention runs a test burst of current through the tissue for a short, ie. less than five seconds, time period, at a low, safe power level. The profile data generated during this period are quickly, i.e. less than five seconds, and automatically programmed into an algorithm that optimizes the voltage, energy, time, and/or power delivery based on the conditions determined during the test period to seal the tissue or organ safely and effectively.

Likewise, the geometry of the jaws/electrodes are optimized for each indication. The length of the jaws and handle segments is optimized for the length of the tissue and location to be sealed and dissected. The force and/or minimum compression gap generated by the jaws is optimized for the tissue selected as well. A minimum force is required to ensure adequate uniform sealing among the entire length of tissue. However, excessive force may result in undesired damage to the tissue and cause significant bleeding prior to the sealing process. The optimal compression force is either predetermined for each organ or the compression handles are designed to exert a predefined force level for a particular organ. In one embodiment of the invention, this is controlled via a slip clutch-type mechanism similar to a torque wrench, or by a travel limiter for the jaws. Thus, there are separate devices designed for each application or once device that could have multiple individual settings that are adjusted to predetermined settings for the organ or thickness of organ to be operated on or removed. In some embodiments, force may be adjusted automatically and dynamically by sensing pressure along the length of one or both jaws with one or more strain gauges associated therewith.

The force exerted by the jaws in other embodiments may be limited by the materials used for the jaws themselves. In the case of an organ or a tissue where the force required to compress and seal the tissue safely is low, a material with a lower flexural modulus may be more appropriate, while in a tissue that can be safely clamped at a higher level to assure effective sealing, a higher modulus material may be used.

In another embodiment, the thickness of the jaws is adjusted by inflating a hollow chamber within the jaws with a pressurized fluid.

The angle between the handles and the jaws of the device may also be optimized to the application. This is determined mainly by the angle of attack of the procedure in the surgical environment. Rather than an abrupt angle, the device may have a gentle or gradual curve for certain applications.

The cutting or dissecting portion of the process may be optimized for specific organs as well. In the case where the cutting is performed by a sharp-edged blade, the width of the blade may vary based on the thickness of the tissue or organ to be removed. The thickness of the cutting material may also be optimized based on how readily the specific thickness/tissue cuts. More tenacious tissue may require more of a saw motion or a thicker or serrated blade or scissor mechanism, which, again, is predetermined for a specific application. If high energy systems are used to dissect the tissue, these may also be optimized for the application, as previously described in the power supply section above.

With regard to a multiple electrode algorithm as taught herein, each electrode is treated independently in terms of energy transmission and RF cycle monitoring, modulation, and termination. The parameters to be monitored in the presently preferred embodiment of the invention are current, voltage, impedance, energy, power, time, and temperature. Any combination of these parameters may be monitored, as well as the values of other parameters. These values may be monitored in a mathematical model that combines them into a single algorithm that determines the quality of the RF sealing process based on prior empirical analysis. The energy and/or power output may be modulated to optimize artery and vein sealing in the shortest time possible, preferably less than one minute, and desirable less than 30 seconds, without excessive heat transmission that could damage surrounding healthy tissue or result in excessive heat that could bond the tissue to the electrode surface. The optimization of the cycle can be based on an algorithm program into the power generator software/firmware that modulates and ultimately terminates the cycle when conditions have been met that have been empirically determined to safely and repeatedly satisfy the conditions of the surgical procedure being performed. For example, reaching a certain impedance and/or temperature value and continuing the power level for a predetermined amount of time beyond this point, or reducing (or conversely increasing) the power level once a certain impedance and pressure or temperature threshold have been reached.

Once desiccation of tissue has occurred, impedance tends to reach a plateau and becomes less of a measure of the quality of the sealing process which occurs after the point that desiccation has begun. Therefore, impedance measurement alone may not be an accurate determinant of successful vessel/tissue sealing. Thus, multiple modulations, step functions, or continuous changes in power, voltage, and/or energy, are provided to optimize the sealing cycle. The cycle changes or modulation may result in upward or downward complex variable changes to optimize the blood vessel/tissue sealing conditions. As a result, each electrode or electrode pair may have different cycle times and power, current, voltage, and energy profiles as a result of the feedback data for the specific segment of tissue contacting the specific electrode. The modulation/determination program may be a complex algorithm based on monitoring multiple variables and responding to a combination of predetermined conditions to adjust and terminate the cycle.

With regards to these variables, the following are typical:
Power 10-1000 watts/channel or electrode pair, typically 100-500 watts/channel or electrode pair;
Impedance 2-500 Ohms, typically 2-200 Ohms;
Voltage 5-500 volts, typically 50-250 volts;
Time space 1-1200 seconds, typically 5-30 seconds; and
Energy 1-30,000 joules, typically 1,000-10,000 joules.

In a presently preferred embodiment, the power generator is comprised of a constant output power design as opposed to a constant voltage or constant current design. In the inventive design, the power output is manifested based upon the load on the system. Thus, if the system sees a very high impedance load, the voltage is maintained at a reasonable level to avoid arcing. In the application to which the power generator is put, i.e. electro-cauterization, the impedance range may vary between, for example, two ohms and 150 ohms during the cauterization of tissue. By applying constant power, the presently inventive power source provides significant current at low impedance to achieve initial desiccation when the tissue is first being cauterized and, as cauterization proceeds, to apply higher voltage to complete the tissue sealing process. Thus, the invention provides larger current and smaller voltage at the beginning of the cauterization process and a higher voltage and lower current at the sealing phase of the process. Control of such power generator only requires that the system monitor power.

In the presently preferred embodiment, the power source is provided with a mechanism for setting the desired power. This can in accordance with a profile or otherwise, as discussed below. Pulse width modulation is used in connection with a flyback transformer. The system charges a primary of the flyback transformer and produces a regulated output. The secondary may be regulated, for example 15 volts at a desired number of amperes to produce the desired power output. Based upon the period, as determined by the width of the pulse which charges the primary, the power curve is determined. Thus, the invention establishes a certain level of power in the primary of the flyback transformer and the same level of power is provided by the secondary without regard to impedance of the load, i.e. the tissue.

Figure 3:
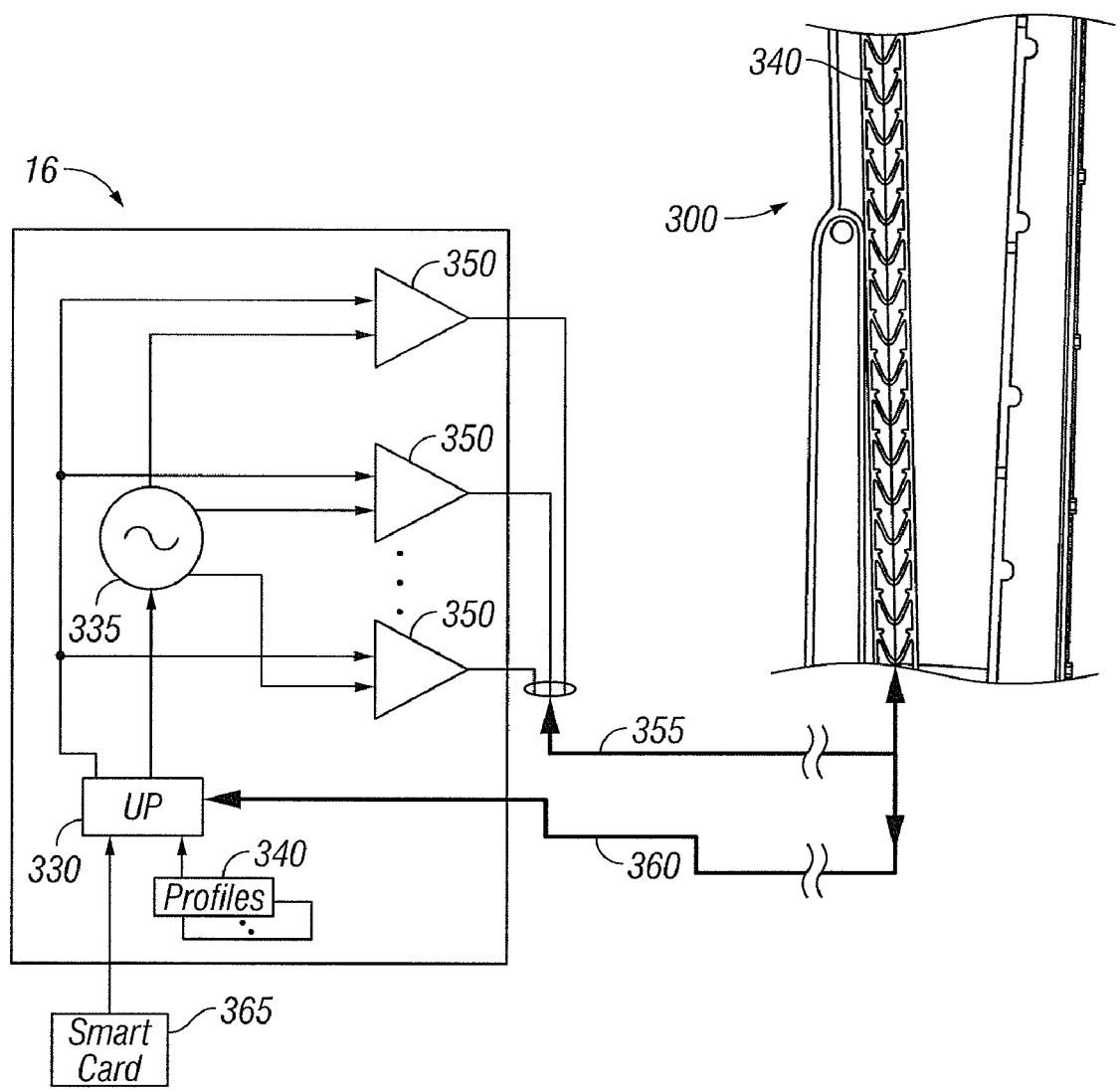
FIG. 3 is a block schematic diagram that illustrates a power generator according to the invention.

In the preferred embodiment invention, the power generator is a source of power for multiple electrodes in the electrical surgical appliance. Accordingly, the power generator is provided with a plurality of output channels, each of which is independently adjustable. In FIG. 3, a block diagram is provided that shows a electrical surgical appliance 300 including a plurality of electrodes 310 as discussed above in connection with FIGS. 1 and 2. The electrical surgical appliance includes a conductive path 55 which typically comprises a plurality of conductors, one for each power generator output channel, for receiving power from power generator 16, and a return path 360 for providing a ground path and/or feedback to a power generator which may comprise any of information concerning current, voltage, impedance, energy, power, and temperature. Appropriate sensors are provided in the electro-surgical appliance. For example, a thermistor can be used to sense temperature, while impedance can be measured between any two or more of the electrodes. Alternatively, a ground plane may be provided on one jaw of the electro-surgical appliance and the individual electrodes may be placed on the other jaw of the electro-surgical appliance, such that a path is provided from and addressed from the electrode through the return electrode. Thus, the one jaw may establish a ground plane for the electrodes that are placed on the other jaw. Additionally, the power generator may be connected to the electrodes at its positive and/or negative terminals. Accordingly, the electronics within the power generator may reassign the polarity and/or use of the various terminals 310 within the appliance in real time. For example, one of the electrodes, or terminals, may be retained as a impedance sensing element. In other embodiments of the invention, this element may be dedicated for purposes of sensing impedance throughout the process.

The power generator 16 is comprised of a power source 335 that has multiple outputs which are controlled by control electronics 50 and thus routed to the individual electrodes in the electro-surgical appliance, as discussed above. The multiple outputs are independently operated by a microprocessor or other control mechanism 330 and are readily modulated and assignable. Thus, an output may be assigned to any one or more of the electrode elements at a certain point in operation of a cauterization cycle, and may be dynamically reassigned at other points of time. For example, if the power source were a four channel power source and the electro-surgical device had 16 electrodes, then each channel may support four electrodes in electro-surgical device. However, this arrangement may altered so that some channels support more electrodes than others.

The microprocessor 330 may be configured through a series of profiles 340 to operate the device with a power curve and power distribution amongst the various electrodes in accordance with the procedure to be performed. Thus, for a hysterectomy a certain profile may be established for the electro-surgical appliance, while for a liver procedure a different profile may be established. Additionally, a smart card reader 365 may be provided that both configures the system for a particular procedure and that provides memory for recording information as to the operation of the power generator during the procedure. For example, the application of power to each channel, impedance sensed, the temperature sensed, and the like is captured to document the procedure.

Figure 4:
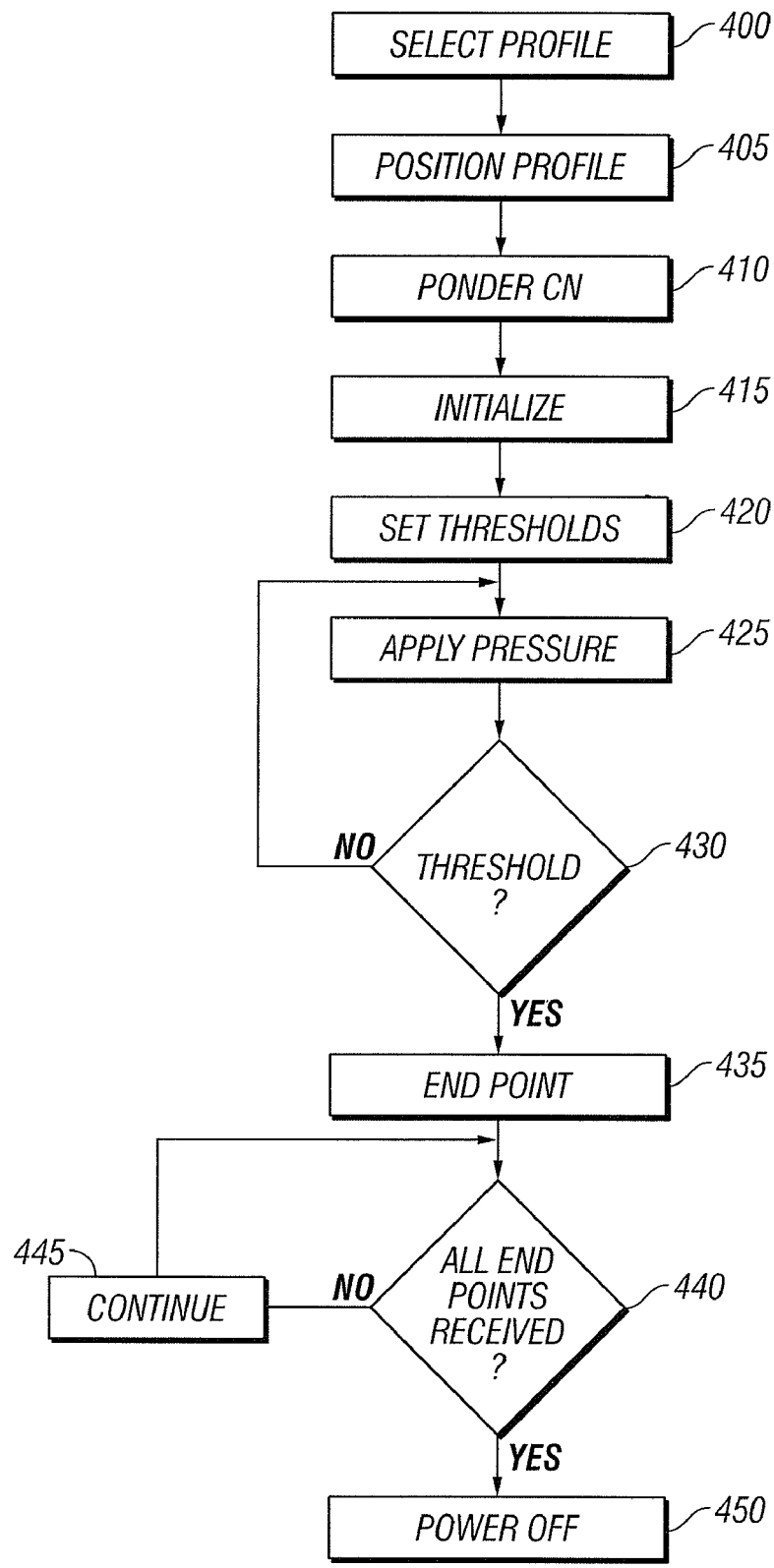
FIG. 4 is a flow diagram showing an algorithm for power modulation according to the invention.

FIG. 4 is a flow diagram showing an algorithm for power modulation according to the invention. At the start of the process, the user determines the profile (400) to be applied for a particular procedure. For example, some tissues or procedures may require a higher initial power level and then provide a reduction in the power level during the cauterization process.

The probe (electro-surgical appliance) is positioned (405) and the power for the power source is turned on (410). The system initializes itself (415), for example by taking initial impedance readings along the various electrodes in the electro-surgical appliance to develop a profile for the tissue to be cauterized. Initialization may also include the taking of initial temperature readings, strain pressure readings which are indicative of the thickness of the tissue along the surgical appliance surface, and other readings. A pilot signal may be transferred through the electro-surgical appliance to determine these values. For example, an initial low voltage may be provided to measure impedance. In this way, a real time profile may be developed for the actual tissue to be cauterized that may be used as an adaptation to the pre-established profile for a particular procedure. Thus, the profile which is established for the procedure may be modified in accordance with measurements related to the tissue to be cauterzied.

The system then sets thresholds (420) which determine when an endpoint is approached. These thresholds may be determined by measurements such as impedance, current, voltage, energy, power, and temperature. The thresholds may also operate in connection with a time element. Thus, when a threshold is reached, the system may continue to operate for a certain period of time to assure that an appropriate endpoint is reached, such that cauterization is complete. In some embodiments, power generator channels that are assigned to electrodes for portions of the tissue that have reached an endpoint may be reassigned to those electrodes that are still actively cauterizing tissue to provide additional power to the process and thus hasten its conclusion.

Power is applied to the electro-surgical appliance (425) to commence cauterization. The system monitors two or more parameters during this process and determines when a threshold is reached (430). Once the threshold is reached, an endpoint procedure (435) is implemented. The endpoint procedure may be as simple as ramping the power down or it may also involve setting a timer. It is important to note that the application of power, while constant across a wide range of impedance may be modulated during the process of cauterization such that a power curve is applied for the procedure. Because the invention provides multiple channels of power for multiple electrodes, some electrodes may reach an endpoint before others. In this case, power to these electrodes is terminated while power is continued to be applied to the other electrodes. Thus, each electrode may have a difference power curve that is modulated in real time. If all endpoints are not reached (440), then the process continues (445); else the power to the system is turned off (450) and the procedure is complete.

The electro-surgical appliance incorporates sensors for capturing various process parameters in real time in accordance with the algorithm. Thus, impedance may be measured between selected electrode pairs or groups of electrodes; temperature may be measured in connection with one or more physical transitions along the surface of the appliance; and the effect of cauterization may be measured with local strain gauges situated along the length of one or both probe jaws (in this embodiment, strain gauges may also be used to precompute a cauterization profile). In this regard, each electrode may be thought of as a separate device which is independently operated for a particular region along the surface of tissue that is contacted by the probe jaws.

Although the invention is described herein with reference to the preferred embodiment, one skilled in the art will readily appreciate that other applications may be substituted for those set forth herein without departing from the spirit and scope of the present invention. For example, in some embodiments the power generator senses whether or not tissue is present at each electrode at the beginning of a cauterization cycle by measuring any of impedance, pressure, or any combination of these and/or other parameters. If for any electrode pair no tissue is present, then such electrode pair is idle and an indication to this effect is provided to a power generator operator. The power generator may also provide a status indicator for each electrode pair is that indicates whether the sealing cycle is active or completed with regard to each electrode pair. In this embodiment, each electrode pair can comprise a mode status indicator, such as an LED for example, that indicates any of an idle, active, or complete condition, once a cauterization cycle is commenced.

Accordingly, the invention should only be limited by the claims included below.

The invention claimed is:

1. An apparatus for cauterizing tissue, comprising:
   a plurality of electrodes for engagement with treatment surfaces of a tissue mass;
   a power supply connectable to said electrodes for selectively applying high frequency power thereto to cauterize tissue between said treatment surfaces, said power supply configured to provide each electrode with a unique power and energy delivery profile based on properties of said tissue in a specific electrode location; and
   at least one sensor proximate to said electrodes and/or proximate to said tissue adapted to generate a signal for controlling said power supply to modulate said high frequency power output from said power supply in real time based upon monitoring of at least two of the following parameters by the at least one sensor:
   current, voltage, impedance, energy, power, temperature, and time
   wherein threshold values associated with said electrodes are set;
   wherein the threshold values are determined to be reached based on said monitoring;
   wherein power continues to be provided to the associated electrodes for a certain period of time such that an appropriate endpoint is reached and to assure that cauterization is complete, when a threshold value of said threshold values is reached; and
   wherein power generator channels, which are assigned to electrodes for portions of the tissue and which have reached endpoints, are reassigned to those electrodes that are still actively cauterizing the tissue.

2. An apparatus as in claim 1, wherein at least one of said electrodes comprises a conformable, electrically conductive surface.

3. An apparatus as in claim 1, wherein at least one of said electrodes comprises a rigid electrically conductive surface.

4. An apparatus for tissue cauterization, comprising:
   a plurality of electrodes for engagement against one or more surfaces of said tissue;
   a power supply having a plurality of channels that are selectively connectable to said electrodes for selectively applying radio frequency energy thereto, said power supply providing multiple, selectable adjustable settings that are based on a tissue to be cauterized, said power supply configured to provide each electrode with a unique power and energy delivery profile based on properties of said tissue in a specific electrode location;
   an automatic feedback system adapted for controlling said radio frequency energy output from said power supply in real time based upon monitoring by said automatic feedback system with a monitoring means of at least two of the following parameters:
   current, voltage, impedance, energy, power, temperature, and time; and
   a control mechanism for supplying radio frequency energy to said electrodes from said power supply to apply said energy to said tissue through said electrodes to selectively energize different ones of said electrodes, and independently applying said power via at least two of said electrodes to said tissue;
   wherein each electrode is treated independently in terms of energy transmission and RF cycle monitoring, modulation, and termination;
   wherein each electrode is configurable to have a difference power curve that is modulated in real time;
   wherein threshold values associated with said electrodes are set by said control mechanism;
   wherein the threshold values are determined to be reached based on said monitoring;
   wherein power continues to be provided to the associated electrodes for a certain period of time such that an appropriate endpoint is reached and to assure that cauterization is complete, when a threshold value of said threshold values is reached; and
   wherein power generator channels, which are assigned to electrodes for portions of the tissue and which have reached endpoints, are reassigned to those electrodes that are still actively cauterizing the tissue.

5. The apparatus of claim 4, further comprising:
   a mathematical model that combines said monitored parameters into an algorithm that determines the quality of tissue sealing based on prior empirical analysis;
   wherein power supply output is modulated to optimize tissue sealing by terminating a cauterization cycle when conditions have been met that have been empirically determined to safely and repeatedly satisfy conditions of a procedure being performed.

6. The apparatus of claim 5, wherein said conditions comprise any of impedance, temperature, pressure, current, voltage, energy, and power; and
   wherein said modulation comprises any of:
   (a) continuing a power level for a predetermined amount of time beyond a predetermined point,
   (b) reducing said power level once a certain condition threshold has been reached, and
   (c) increasing said power level once a certain condition threshold has been reached.

7. The apparatus of claim 5, wherein each electrode has any of different cycle times and power, current, voltage, and energy profiles as a result of feedback data for a specific segment of tissue contacting a specific electrode.

8. The apparatus of claim 4, said power supply further comprising:
   a constant output power circuit.

9. The apparatus of claim 4, said control mechanism operable for setting a desired power in accordance with a profile.

10. The apparatus of claim 4, wherein each channel of said plurality of channels is independently adjustable to provide a source of power for each of said electrodes.

11. The apparatus of claim 4, said monitoring means further comprising:
    one or more sensors.

12. The apparatus of claim 4, wherein said power supply is configured by one or more profiles to operate with a power curve and power distribution amongst said electrodes in accordance with a desired cauterization procedure.

13. The apparatus of claim 4, further comprising:
a smart card reader for reading a smart card for use in configuring said power supply for a particular cauterization procedure, and for recording information indicative of operation of the power supply during said cauterization procedure.

14. The apparatus of claim 4, said power supply further comprising:
means for capturing a real time profile of the tissue to be cauterized; and
said control mechanism using said real time profile to adapt a pre-established profile for a particular cauterization procedure;
wherein the profile which is previously established for the particular cauterization procedure is modified in accordance with the real time profile of the tissue to be cauterized.

15. The apparatus of claim 4, said monitoring means further comprising:
sensors for monitoring two or more of said parameters during cauterization and for determining when a threshold is reached.

16. The apparatus of claim 15, wherein once said threshold is reached, an endpoint procedure is implemented.

17. The apparatus of claim 4, said monitoring means further comprising:
at least one sensor for measuring temperature in connection with one or more physical transitions along a surface of an appliance associated with one or more of said electrodes.

18. The apparatus of claim 4, said automatic feedback system further comprising:
local strain gauges situated along a length of at least one probe jaw associated with one or more of said electrodes for measuring the effect of cauterization.

19. The apparatus of claim 18, wherein said strain gauges provide information that is used to precompute a cauterization profile.

20. The apparatus of claim 4, said monitoring means further comprising:
sensors for sensing at the beginning of a cycle whether tissue is present at each electrode;
wherein when any adjacent or opposing two of said electrodes have no tissue present said electrodes become idle and said power supply indicates which electrodes, if any, are idle.

21. The apparatus of claim 20, said power supply further comprising:
an indicator for each electrode pair that provides status of a cauterization cycle that is indicative of whether said cycle is active or completed.

22. The apparatus of claim 21, wherein a mode status indicator is provided for each electrode to indicate any of an idle, active, and completed condition, once a cycle is commenced.

* * * * *